(12) United States Patent
Goldenberg et al.

(10) Patent No.: US 9,745,374 B2
(45) Date of Patent: *Aug. 29, 2017

(54) FUSION PROTEINS CONTAINING RECOMBINANT CYTOTOXIC RNASES

(75) Inventors: David M. Goldenberg, Mendham, NJ (US); Hans J. Hansen, Picayune, MS (US); Chien-Hsing Ken Chang, Downingtown, PA (US); Sailaja S. Vanama, Monroe, NJ (US); Edmund A. Rossi, Nutley, NJ (US)

(73) Assignee: IMMUNOMEDICS, INC., Morris Plains, NJ (US)

( * ) Notice: Subject to any disclaimer, the term of this patent is extended or adjusted under 35 U.S.C. 154(b) by 184 days.

This patent is subject to a terminal disclaimer.

(21) Appl. No.: 13/402,480

(22) Filed: Feb. 22, 2012

(65) Prior Publication Data

US 2012/0149085 A1 Jun. 14, 2012

Related U.S. Application Data

(60) Division of application No. 12/479,250, filed on Jun. 5, 2009, now Pat. No. 8,192,739, which is a continuation of application No. 11/056,182, filed on Feb. 14, 2005, now Pat. No. 7,544,487.

(60) Provisional application No. 60/544,227, filed on Feb. 13, 2004.

(51) Int. Cl.
*A61K 47/48* (2006.01)
*C07K 16/28* (2006.01)
*C07K 16/30* (2006.01)
*C12N 9/12* (2006.01)
*C12N 9/22* (2006.01)

(52) U.S. Cl.
CPC .... *C07K 16/2803* (2013.01); *A61K 47/48438* (2013.01); *A61K 47/48669* (2013.01); *C07K 16/2833* (2013.01); *C12N 9/22* (2013.01); *C07K 2317/24* (2013.01); *C07K 2317/41* (2013.01); *C07K 2319/00* (2013.01); *C07K 2319/33* (2013.01); *C12N 2510/02* (2013.01)

(58) Field of Classification Search
CPC ........ A61K 47/48438; A61K 47/48669; C07K 16/00; C07K 16/2803; C07K 16/2896; C07K 16/3007; C07K 16/2833; C07K 2317/24; C07K 2317/41; C07K 2319/00; C07K 2319/33; C07K 2319/55; C12N 9/22; C12N 2510/02
See application file for complete search history.

(56) References Cited

U.S. PATENT DOCUMENTS 5,650,150 A 7/1997 Gillies
6,045,793 A 4/2000 Rybak et al.
6,472,511 B1 10/2002 Leung et al.
8,192,739 B2 * 6/2012 Goldenberg et al. ...... 424/133.1
2003/0099629 A1 5/2003 Goldenberg et al.
2004/0001825 A1 * 1/2004 Govindan et al. ......... 424/141.1

OTHER PUBLICATIONS

Roitt et al., p. 5.8 and 5.9, in Immunology second edition, Gower Medical Publishing New York 1989.*
Jubala et al., Vet Pathol 42: 468-476, 2005.*
Yu et al., Investigative Ophthalmology & Visual Science 49(2): 522-527, Feb. 2008.*
Witte et al., Cancer and Metastasis Reviews 17: 155-161, 1998.*
Dosio et al., Toxins 3: 848-883, 2011.*
Youle, Richard J., et al., "Cytotoxic Ribonucleases and Chimeras in Cancer Therapy", Critical Reviews in Therapeutic Drug Carrier Systems, 10(1):1-28(1993).
Rybak, Susanna M., et al., "Rational Immunotherapy with Ribonuclease Chimeras", Cell Biophysics, vol. 21, 1992, p. 121-138.
Rybak, Susanna M., et al., "Humanization of Immunotoxins", 6039 Proceedings of the National Academy of Sciences of the USA 89 (1992) Apr. 15, No. 8, Washington, DC, US, pp. 3165-3169.
Newton, Dianne L., et al., "Potent and specific antitumor effects of an anti-CD22-targeted cytotoxic ribonuclease: potential for the treatment of non-Hodgkin lymphoma", Blood, Jan. 15, 2001, vol. 97, pp. 528-535.
Notomista, Eugenio, et al., "Effective expression and purification of recombinant onoconase, an antitumor protein", FEBS Letters vol. 463: 211-251, 1999.
Liao, You-Di, et al., "The structural integrity exerted by N-terminal pyroglutamate is crucial for the cytotoxicity of frog ribonuclease from Rana pipiens", Nucleic Acids Research, 2003, vol. 31, No. 18 5247-5255.
Chang, Chien-Hsing, et al., "Effective therapy of human lymphoma xenografts with a novel recombinant ribonuclease/anti-CD74 humanized IgG4 antibody immunotoxin", Blood, Dec. 15, 2005, vol. 106, No. 13, pp. 4308-4314.
Stocker, et al., Protein Expression and Purification 28: 211-219; Apr. 2003.
Schuurman, et al., Molecular Immunology 38:1-8, 2001.
Rudikoff, et al., Proc Natl Acad Sci USA 79: 1979, 1982.
Barrios, et al., J. Molecular Recognition 17:332-338, 2004.

* cited by examiner

*Primary Examiner* — Phuong Huynh
(74) *Attorney, Agent, or Firm* — Rossi, Kimms & McDowell LLP

(57) ABSTRACT

Recombinant immunotoxins containing a cytotoxic RNAse fused to an antibody or antibody fragment may be produced in mammalian cell culture. Surprisingly, immunotoxins containing a cytotoxic RNAse fused to the N-terminus of one antibody variable domain can be prepared and retain the ability to specifically bind antigen. The immunotoxins may be used in a variety of therapeutic methods for treating diseases or syndromes associated with unwanted or inappropriate cell proliferation or activation.

16 Claims, 14 Drawing Sheets

FUSION PROTEINS CONTAINING RECOMBINANT CYTOTOXIC RNASES

This application is a divisional of U.S. patent application Ser. No. 12/479,250 filed Jun. 5, 2009, which is a continuation of U.S. patent application Ser. No. 11/056,182, filed Feb. 14, 2005, now U.S. Pat. No. 7,544,487, which is a U.S. non-provisional application based on U.S. Provisional application Ser. No. 60/544,227, filed Feb. 13, 2004. The contents of all of the aforementioned applications are hereby incorporated by reference in their entirety.

BACKGROUND OF THE INVENTION

The present invention provides immunotoxins comprising fusion proteins of non-mammalian cytotoxic RNAses and immunoglobulins and immunoglobulin fragments.

Ranpirnase is a member of a class of non-mammalian ribonucleases (RNAses) that show promise as cyotoxic agents for the treatment of disease. The cytotoxicity of these RNAses has been attributed to a mechanism that involves initial binding to cell surface receptors and internalization to the cell cytosol, with concomitant degradation of ribosomal RNA and inhibition of cellular protein synthesis. See Wu et al., *J. Biol. Chem.*, 268:10686-10693 (1993). The RNAse activity is resistant to mammalian RNAse inhibitors, which may explain the enhanced cytotoxicity that is observed compared to the mammalian enzymes. Id. Ranpirnase is the prototypic member of this family of RNAses, and can be purified from Rana pipiens oocytes and early embryos. Ranpirnase has a molecular weight of 12,000 and causes potent inhibition of protein synthesis in the rabbit reticulocyte lysate ($IC_{50}$ $10^{-11}$ M) and when microinjected into *Xenopus* oocytes ($IC_{50}$ $10^{-10}$ M). Unlike other members of the RNase A superfamily, these cytotoxic ribonucleases do not degrade oocyte rRNA. Lin et al., *Biochem Biophys Res Commun.* 204:156-62 (1994). These molecules contain an obligate N-terminal pyroglutamyl residue that forms part of the phosphate binding pocket of the enzyme, and that is essential for RNAse and anti-tumor activity.

Animal toxicology studies show that ranpirnase displays a predictable, dose-dependent and reversible toxicity in both rats (dose range 0.01-0.02 mg/kg) and dogs (0.005-0.15 mg/kg). Mice inoculated with the aggressive M109 Madison lung carcinoma and treated with both daily and weekly schedule of intraperitoneally administered ranpirnase, showed significantly prolonged survival. Most striking results were seen in a group of mice treated with a weekly schedule of ranpirnase in which six of eighteen animals survived long-term and were apparently cured of cancer. Mikulski et al. *J Natl Cancer Inst.* 82:151-3 (1990).

Native ranpirnase has been shown in clinical trials to have anti-tumor activity against a variety of solid tumors. In this regard it has been used both alone and combined with other anti-tumor agents such as tamoxifen, e.g., when treating patients with pancreatic cancer. When used as an anti-tumor agent, these cytotoxic RNAses can be conjugated to a marker to permit targeting to a specific cell type.

In a Phase I study, patients suffering from a variety of relapsing and resistant tumors were treated intravenously on a weekly basis with ranpirnase (dosage range 60-960 $\mu g/m^2$). Side effects observed included flushing, myalgias, transient dizziness, and decreased appetite in general. The observed toxicities, including the dose-limiting renal toxicity manifested by increasing proteinuria, peripheral edema, azotemia, a decreased creatinine clearance, as well as fatigue, were dose-dependent and reversible, which is in agreement with the animal toxicology studies. No clinical manifestation of a true immunological sensitization was evident, even after repeated weekly intravenous-doses of ranpirnase. The maximum tolerated dose, mainly due to renal toxicity, was found to be 960 $\mu g/m^2$. There were also some objective responses in non-small cell lung, esophageal, and colorectal carcinomas. See Mikulski et al., *Int J Oncol* 3:57-64, (1993); Mikulski et al. *J Clin Oncol.* 20:274-81 (2002). Nevertheless, ranpirnase was well-tolerated by animals and the majority of human patients tested, demonstrated a consistent and reversible clinical toxicity pattern, and did not induce most of the toxicities associated with most conventional chemotherapeutic agents, such as myelosuppression and alopecia.

WO 97/31116 discloses a recombinant ribonuclease having (a) an N-terminal methionine followed by an amino acid other than glutamic acid, (b) a cysteine at positions 26, 40, 58, 84, 95 and 110, a lysine at position 41, and a histidine at position 119 (as aligned for maximum correspondence with bovine RNAse A), and a native ranpirnase-derived amino acid sequence. Recombinant cytotoxic RNAses, including RNAse variants, have, however, been prepared in bacteria by a multi-step process that requires additional steps to remove the N-terminal formylmethione residue inserted by the bacteria and to generate the obligate N-terminal pyroglutamyl residue. Nevertheless, production in bacteria precludes the preparation of glycosylated cytotoxic RNAse-containing fusion proteins. Accordingly, it would be advantageous to produce a recombinant cytotoxic RNAse fusion protein in eukaryotic cells where the cytotoxic RNAse retains the cytotoxic properties of ranpirnase purified from amphibian sources, but that has fewer, or no, undesirable immune responses in humans. However, it also would be expected that expression of cytotoxic RNAse in eukaryotic cells would result in cell death due to the cytotoxic activity of the RNAse.

It is apparent, therefore, that improved methods of preparing cytotoxic RNAse-containing fusion proteins, including glycosylated RNAse fusion proteins, are greatly to be desired. It also is apparent that glycosylated cytotoxic RNAse fusion proteins themselves are highly desirable molecules.

SUMMARY OF THE INVENTION

It is therefore an object of the present invention to provide an immunotoxin comprising (a) a fusion polypeptide, where the fusion protein contains a non-mammalian cytotoxic ribonuclease fused to a first immunoglobulin variable domain and (b) a second polypeptide comprising a second immunoglobulin variable domain, where one of the immunoglobulin variable domains is a light chain variable domain and the other immunoglobulin variable domain is a heavy chain variable domain, where the first and second immunoglobulin variable domains together form an antigen binding site, and where the immunotoxin is glycosylated.

It is another object of the invention to provide methods of making these and other immunotoxins by culturing a mammalian host cell, where the host cell is transformed with (a) a nucleic acid sequence encoding a fusion polypeptide, where the fusion polypeptide contains a non-mammalian cytotoxic ribonuclease fused to a first immunoglobulin variable domain and (b) a nucleic acid sequence encoding a second polypeptide contains a second immunoglobulin variable domain, where the first and second immunoglobulin variable domains together form an antigen binding site.

It is yet another object of the invention to provide an immunotoxin containing an internalizing antibody or antibody fragment fused to a cytotoxic RNAse moiety, where the RNAse moiety bears an N-terminal pyroglutamate residue and is fused at its C-terminus to the N-terminus of a polypeptide containing the light chain of the antibody or antibody fragment, or to the N-terminus of a polypeptide containing the heavy chain of the antibody or fragment, or to the N-termini of both the light and the heavy chains of the antibody or fragment.

For example, in one embodiment, the non-mammalian cytotoxic ribonuclease may be fused to the N-terminus of the first immunoglobulin variable domain, for example, a light chain variable domain. The non-mammalian ribonuclease may have an N-terminal pyroglutamate residue.

The fusion polypeptide and the second immunoglobulin variable domain may be separate molecules and may be produced as separate molecules in the host cell.

The fusion polypeptide may further contain a CL domain and the second polypeptide may further contain a CH1 domain.

The second polypeptide may further contain a CH2 domain and a CH3 domain.

In another embodiment, the non-mammalian ribonuclease may be fused to the N-terminus of a heavy chain variable domain. The non-mammalian ribonuclease may have an N-terminal pyroglutamate residue. The fusion polypeptide and the second immunoglobulin variable domain may be separate molecules and may be produced as separate molecules in the host cell.

The fusion polypeptide may further contain a CH1 domain and the second polypeptide may further contain a CL domain.

The fusion polypeptide may further contain a CH2 domain and a CH3 domain.

In still another embodiment, the non-mammalian ribonuclease may be fused to the N-terminus of both the first and second immunoglobulin variable domains. The non-mammalian ribonuclease may have an N-terminal pyroglutamate residue. The first immunoglobulin variable domain may be a heavy chain variable domain and the second immunoglobulin variable domain may be a light chain variable domain The first and second fusion polypeptides may be separate molecules and may be produced as separate molecules in the host cell.

The first fusion polypeptide may further contain a CH1 domain and the second fusion polypeptide may further contain a CL domain.

The first fusion polypeptide may further contain a CH2 domain and a CH3 domain.

The immunotoxin may be glycosylated, for example on the CH2 domain and/or on the RNAse.

The non-mammalian cytotoxic ribonuclease may be an enzyme, for example, having the sequence and structure of ranpirnase purified from *Rana pipiens*.

The antigen binding site may bind specifically to a cell-surface molecule and the immunotoxin may be internalized upon binding to a cell bearing the cell-surface molecule.

The immunotoxin may be directed against cancer cells, sites of infection/inflammation, autoimmune diseases, or against microorganisms and parasites.

The immunotoxin may be directed against an antigen selected from the group consisting of tumor-associated antigens, including B-cell antigens, T-cell antigens, plasma cell antigens, HLA-DR lineage antigens, CEA, NCA, MUC1, MUC2, MUC3, MUC4 and MUC16 antigens, EGP-1 antigens, EGP-2 antigens, placental alkaline phosphatase antigen, IL-6, VEGF, PlGF, ILGF, EGFR, Her2/neu, tenascin, CD33, CD74, PSMA, PSA, PAP, Le$^y$, antigens associated with autoimmune diseases, infection/inflammation, and infectious diseases.

The antigen may be a target antigen associated with a B- or T-cell lymphoma, or B- or T-cells associated with autoimmune diseases.

The antigen may be an antigen selected from the group consisting of CD19, CD22, CD40, CD74, CEA, NCA, MUC1, MUC2, MUC3, MUC4, HLA-DR, EGP-1, EGP-2, EGFR, Her2/neu, IL-15 and HLA-DR expressed by malignant diseases.

The immunoglobulin variable domains of the immunotoxin may be derived, for example, from RS11, 17-1A, RS7, LL1, LL2, MN-3, MN-14, MN-15 or PAM4, or humanized versions thereof, when targeting malignant diseases.

The antigen that is bound by the immunotoxin may be, for example EGP-2, EGP-1, CD22, CD74, CEA, carbonic anhydrase IX, or MUC 1, for certain malignant diseases.

The targeted antigens may be expressed by bacteria, viruses, fungi, mycoplasma, parasites, or other microorganisms.

The targeted antigens may be expressed by the host cells accumulating at the sites of infection, such as activated granulocytes (e.g., CD15, CD33, CD66a, CD66b, and CD66c (NCA), etc.). A suitable such granulocyte antibody is MN-3, whose Fab' is used in LeukoScan®.

In any of the above methods and/or compositions the variable domains may be humanized or human domains.

In another embodiment of the invention there is provided a pharmaceutical composition containing an immunotoxin as described above together with a pharmaceutically acceptable carrier.

In still another embodiment of the invention there is provided a method of treating a disease or syndrome in a subject, by administering to the subject a composition as described above in an amount that is effective to treat or ameliorate the symptoms of the disease or syndrome. The disease or syndrome may be characterized by unwanted or inappropriate proliferation or activation of cells in the subject, for example, T-cells, myeloid cells, or plasma cells. Alternatively, the disease may be characterized by the presence of an infectious microorganism or parasite.

The disease may be selected, for example, from the group of cancers consisting of carcinomas, sarcomas, gliomas, leukemias, lymphomas, melanomas, neuroblastomas and myelomas.

The disease or syndrome may be characterized by the presence of a solid tumor, such as neuroblastoma, malignant melanoma, or carcinomas, such as breast, ovarian, prostate, lung, kidney, stomach, colorectal, liver or pancreatic carcinomas.

In these methods the pharmaceutical composition may be administered to the subject more than once, in an amount, for example of 0.1 to about 1000 mg per day, although more or less could be used.

The cells undergoing unwanted or inappropriate proliferation or activation may be involved in the development and progression of one or more autoimmune diseases, such as for example, rheumatoid arthritis, Sjögren's syndrome, acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, poly glandular syndromes, bullous pemphigoid, diabetes mellitus, Henoch- Schonlein purpura, post-streptococcal nephritis, erythema nodosum, Takayasu's arteritis, Addison's disease, multiple sclerosis, sarcoidosis, ulcerative colitis, erythema multiforme, IgA nephropathy, polyarteritis nodosa, ankylosing spondylitis, Goodpasture's syndrome, thromboangitis ubiterans, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

When the compositions of the present invention are used for the therapeutic treatment of infections, the immunoglbulin component of the immunotoxin may specifically binds to a disease-causing microorganism, such as pathogenic bacteria, viruses, fungi and diverse parasites, and the antibody can target these microorganisms, their products or surface antigens, or antigens associated with their lesions. Examples of microorganisms include, but are not limited to:

*Streptococcus agalactiae, Legionella pneumophilia, Streptococcus pyogenes, Escherichia coli, Neisseria gonorrhosae, Neisseria meningitidis,* Pneumococcus, Hemophilis influenzae B, *Treponema pallidum,* Lyme disease spirochetes, *Pseudomonas aeruginosa, Mycobacterium leprae, Brucella abortus, Mycobacterium tuberculosis,* Tetanus toxin, Anti-viral MAbs, HIV-1,-2,-3, Hepatitis A, B, C, D, Rabies virus, Influenza virus, Cytomegalovirus, Herpes simplex I and II, Human serum parvo-like virus, Respiratory syncytial virus, Varicella-Zoster virus, Hepatitis B virus, Measles virus, Adenovirus, Human T-cell leukemia viruses, Epstein-Barr virus, Murine leukemia virus, Mumps virus, Vesicular stomatitis virus, Sindbis virus, Lymphocytic choriomeningitis virus, Wart virus, Blue tongue virus, Sendai virus, Feline leukemia virus, Reo virus, Polio virus, Simian virus 40, Mouse mammary tumor virus, Dengue virus, Polyoma virus, Papilloma viruses, SARS virus, various Influenza viruses, Rubella virus, protozoa, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma, Mycoplasma arthritidis, M. hyorhinis, M. orale, M. arginini, Acholeplasma laidlawii, M. salivarium,* and *M. pneumoniae.*

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

Figure 1:
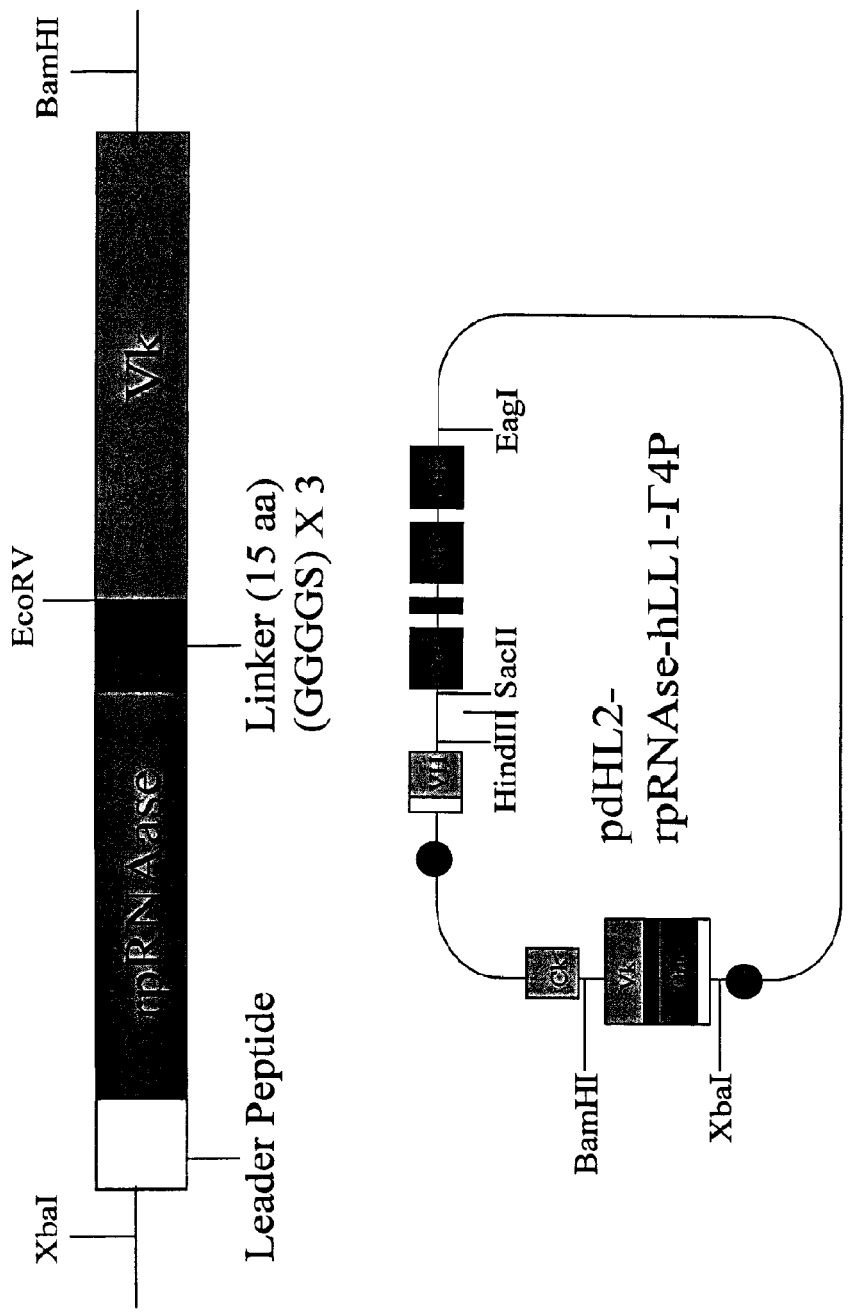
FIG. 1 shows construction of the vector pdHL2-rap-hLL1-γ4P. An XbaI-BamHI fragment containing the construct Leader peptide-RNAse,-Linker-Vk region of hLL1 was inserted into the pBS vector and ligated into the pdHL2 vector. Note: in the context of this application, the terms rpRNAse and rap are interchangeable ((GGGGS)$_3$ linker is disclosed as SEQ ID NO: 17).

The inventors surprisingly have found fusion molecules containing a cytotoxic RNAse molecule can be prepared in mammalian cells. This result is surprising because a molecule containing an enzymatically active cytotoxic RNAse molecule would be expected to be cytotoxic to an extent that would preclude cell growth and would thereby prevent recombinant production of the fusion protein.

This result provides possibilities for preparing cytotoxic RNAse-fusion proteins in mammalian cells that previously would have been difficult or impossible to prepare by recombinant methods using prokaryotic host cells. For example, production in mammalian host cells avoids the difficulties associated with generating the obligate N-terminal pyroglutamyl residue when using prokaryotic host cells. Moreover, use of mammalian host cells permits the facile preparation of multi-subunit proteins, such as IgG structures containing an intact Fc region, and also permits preparation of glycosylated fusion proteins, such as intact antibodies that are glycosylated on the Fc region. Fusion proteins between a cytotoxic RNAse and an immunoglobulin, such as an antibody or antibody fragment, are hereinafter referred to as immunotoxins. The method also may be used for preparing immunotoxins containing any suitable antibody fragment, such as F(ab')$_2$, F(ab)$_2$, Fab' Fab, Fv and scFv.

The invention also provides cytotoxic RNAse-containing immunoglobulin fusion proteins where the RNAse is fused to the N-terminus of one of the Ig variable domains, for example the VH or VL domains. This surprisingly provides fusion proteins that not only retain cytotoxic RNAse activity but that retain the Ig binding specificity at the antigen binding site, which would have been expected to be sterically blocked by preparation of an N-terminal fusion.

In addition the inventors surprisingly have found that the cytotoxic RNAse fusion proteins of the invention are effective at killing cells and microorganisms/parasites. In particular, it has been found that immunotoxins that contain a rapidly internalizing antibody component are highly cytotoxic in a cell-specific manner. For example, fusion of a cytotoxic RNAse to the N-terminus of a humanized LL1 antibody produced an immunotoxin that bound specifically to cells expressing the invariant chain of CD74 (the target of LL-1) and was cytotoxic to that cell population upon binding. This result is surprising because the fusion protein would be expected to be delivered into, and degraded in, the lysosome of the cell upon internalization, which would have been expected to greatly reduce or, more likely eliminate, the cytotoxicity of the fusion protein.

The invention also provides methods of treating a subject suffering from a disease or a syndrome by administering to the subject an effective amount of an immunotoxin of the type described above.

Definitions

Unless otherwise defined, all technical and scientific terms used have the same meaning as commonly understood by one of ordinary skill in the art. In addition, the contents of all patents and other references cited herein are incorporated by reference in their entirety. For purposes of the present invention, the following terms are defined as follows:

Amino acids are referred to by name or by either their commonly known three-letter symbols or by the one-letter IUPAC symbols. Nucleotides are referred to by their commonly accepted single-letter codes.

"Conservatively modified variations" of a particular nucleic acid sequence refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Each codon in a nucleic acid except AUG which encodes methionine can be modified to yield a functionally identical molecule. The nucleic acid sequences described herein also encompass these alterations.

"Conservatively modified variations" of an amino acid sequence include individual substitutions which alter a single amino acid or a small percentage of amino acids in an encoded sequence, where the alterations result in the substitution of an amino acid with a chemically similar amino acid. Conservative substitutions are well known to those of skill in the art. The following six groups each contain amino acids that are conservative substitutions for one another:

1. Alanine, Serine, Threonine
2. Aspartic acid, Glutamic Acid
3. Asparagine, Glutamine
4. Arginine, Lysine
5. Isoleucine, Leucine, Methionine, Valine, and
6. Phenylalanine, Tyrosine, Tryptophan.

"Conservatively modified variations" of an amino acid sequence also include deletions or additions of a single amino acid or a small percentage of amino acids in an encoded sequence, where the additions and deletions result in the substitution of an amino acid with a chemically similar amino acid. The amino acid sequences described herein also encompass these variations.

The terms "isolated" or "biologically pure" refer to material which is substantially or essentially free from components which normally accompany it as found in its naturally occurring environment. The isolated material optionally comprises material not found with the material in its natural environment.

The term "nucleic acid" refers to a deoxyribonuclease or ribonucleotide polymer in either single- or double-stranded form and, unless otherwise limited, encompasses known analogues of natural nucleotides that hybridize to nucleic acids in a manner similar to naturally occurring nucleotides. Unless otherwise indicated, a particular nucleic acid sequence includes its complementary sequence.

An "expression vector" includes a recombinant expression cassette which includes a nucleic acid which encodes a polypeptide according to the invention which can be transcribed and translated by a cell. A recombinant expression cassette is a nucleic acid construct, generated recombinantly or synthetically, with a series of specified nucleic acid elements which permit transcription of a particular nucleic acid in a target cell. The expression vector can be part of a plasmid, virus, or nucleic acid fragment. Typically, the recombinant expression cassette portion of the expression vector includes a nucleic acid to be transcribed and a promoter operably linked thereto.

The term "recombinant" when used with reference to a protein indicates that a cell expresses a peptide or protein encoded by a nucleic acid whose origin is exogenous to the cell. Recombinant cells can express genes that are not found within the native (non-recombinant) form of the cell. Recombinant cells also can express genes found in the native form of the cell wherein the genes are re-introduced into the cell by artificial means, for example, under the control of a heterologous promoter.

The term "substantial identity" or "substantial similarity" in the context of a polypeptide indicates that a polypeptide comprises a sequence with at least 80%, more preferably 90%, and most preferably at least 95% identity with a reference sequence. Two polypeptides that are substantially identical means the one of the polypeptides is immunologically reactive with antibodies raised against the second peptide. Two nucleic acids are substantially identical is the two molecules hybridize to each other under stringent conditions. Generally, stringent conditions are selected to be about 5.degree. C. to 20.degree. C. lower than the thermal melting point ($T_m$) for a specific sequence at a defined ionic strength and pH. The Tm is the temperature (under defined ionic strength and pH) at which 50% of the target sequence hybridizes to a perfectly matched probe. However, nucleic acids that do not hybridize to each other under stringent conditions are still substantially identical if the polypeptides they encode are substantially identical.

An "antibody" includes both whole antibodies of various immunoglobulin species ($IgG_1$, $IgG_4$, IgM, etc.) and antibody fragments well known in the art, such as $F(ab')_2$, $F(ab)_2$, Fab', Fab, Fv and the like, including hybrid fragments that retain the ability to bind a target antigen. Also useful are any subfragments that retain the hypervariable, antigen-binding region of an immunoglobulin. Methods of making antibody fragments from whole antibodies where the fragments retain the ability to specifically bind antigen are well known in the art and are described, for example in Harlow and Lane "Antibodies: A Laboratory Manual," CSHL Press (1988). Methods of making recombinant antibodies or antibody fragments also are well known in the art and are described, for example, in McCafferty et al. "Antibody Engineering: A Practical Approach" IRL Press (1996). A Fab fragment contains a (VL-CL)-(VH-CH1) dimer that typically contains an interchain disulfide bond. A Fab' fragment is similar but also contains part of the heavy chain hinge domain. A $F(ab')_2$ fragment is conventionally understood to refer to a disulfide linked dimer of two Fab' fragments. An antibody of the present invention may be of any species, although advantageously the antibody is a human or humanized antibody. The antibody also may be any of the well known forms or recombinant antibody, such as single chain Fv (containing a VL chain linked by an optional linker to a VH chain). When the linker is short or absent the single chain Fv dimerizes to a dimer or multimer, where the dimer is known as a diabody. Under certain circumstances the antibody of the invention also may include a single binding domain antibody, such as a camelid antibody (see Dumoulin et al. "Single-domain antibody fragments with high conformational stability." *Protein Sci.* 11, 500-515 (2002); Hamers-Casterman et al. "Naturally occurring antibodies devoid of light chains" *Nature* 363, 446-448 (1993); and Muyldermans. "Single domain camel antibodies: current status" *J Biotechnol.* 74, 277-302 (2001)) or a "domain antibody." See WO92/01787 and references cited therein. A human antibody is an antibody or antibody fragment that has a sequence that is either derived from an antibody produced in a human subject or that has a sequence that is characteristic of antibodies produced in humans. Such antibodies are described, for example, in U.S. Pat. No. 6,300,064. Human antibodies also can be isolated from human antibody libraries. See, for example, U.S. Pat. Nos. 6,300,064 and 6,172,197 and reference described therein. A humanized antibody is an antibody prepared by inserting CRD regions from a non-human antibody into a human framework, optionally followed by mutation of certain framework residues to restore or optimize antigen binding. Humanized antibodies are well known in the art and are described, for example, in Jones et al., *Nature* 321:522 (1988); Riechmann et al., *Nature* 332:323 (1988); and Winter & Milstein, *Nature,* 349:293 (1991)

A "targeting moiety" is an antibody, peptide, cytokine, oligonucleotide, or growth factor that is specific to a marker or receptor on a given cell type. A targeting moiety can be used to specifically deliver an attached molecule to a given cell type, by preferentially associating with the marker associated with that cell type.

A "fusion protein" is a chimeric molecule formed by joining two or more polypeptides, more particularly, a cytotoxic RNAse and a targeting moiety. The cytotoxic RNAse and the targeting moiety are joined through a peptide bond formed between the amino terminus of the targeting moiety and the carboxyl terminus of the RNAse, and are expressed recombinantly by a nucleic acid sequence encoding the fusion protein. A single chain fusion protein is a fusion protein that has a single contiguous polypeptide backbone.

A "chemical conjugate" is a conjugate formed by the chemical coupling of a cytotoxic RNAse and a targeting moiety.

"A pharmaceutically acceptable carrier" is a material that can be used as a vehicle for administering the immunotoxin because the material is' inert or otherwise medically acceptable, as well as compatible with the fusion protein or armed ligand.

Preparation of Cytotoxic RNAse-encoding Nucleic Acids

The skilled artisan will recognize that the cytotoxic RNAse moieties suitable for use in the present invention include polypeptides having a native ranpirnase structure and all enzymatically active variants thereof. These molecules advantageously have an N-terminal pyroglutamic acid resides that appears essential for RNAse activity and are not substantially inhibited by mammalian RNAse inhibitors. Nucleic acid that encodes a native cytotoxic RNAse may be prepared by cloning and restriction of appropriate sequences, or using DNA amplification with polymerase chain reaction (PCR). The amino acid sequence of *Rana Pipiens* ranpirnase can be obtained from Ardelt et al., *J. Biol. Chem.,* 256: 245 (1991), and cDNA sequences encoding native ranpirnase, or a conservatively modified variation thereof, can be gene-synthesized by methods similar to the en bloc V-gene assembly method used in hLL2 humanization. Leung et al., *Mol. Immunol.,* 32: 1413 (1995). Methods of making cytotoxic RNAse variants are known in the art and are within the skill of the routineer.

Alternatively, nucleic acid that encodes a cytotoxic RNAse or variant thereof may be synthesized in vitro. Chemical synthesis produces a single-stranded oligonucleotide. This may be converted to a double-stranded DNA by hybridization with a complementary sequence, or by polymerization with a DNA polymerase using a short primer and the single strand as a template. While chemical synthesis is most suited to sequences of about 100 bases, longer sequences may be obtained by ligating shorter sequences. Example 2, infra, provides one illustrative method for obtaining a cytotoxic RNAse gene.

Preparation of Immunoglobulin Genes

Methods of preparing antibody-encoding genes are well known in the art. For example, PCR using degenerate primer sets may be used to amplify variable chain sequences cDNA obtained from antibody-producing cells, such as hybridomas (or direct RT-PCR using well-known methods may be used directly on mRNA obtained from the cells.) See, for example, Marks et al., *J Mol Biol.* (1991) 222:581-97 and references cited therein. Non-human antibodies may be humanized by methods that are well known in the art. See Leung, supra, and methods cited therein. Alternatively, genes encoding human (or other species) antibody variable domains may be obtained from phage display libraries of the type commercially available from MorphoSys (Martinsried, Germany) or Cambridge Antibody Technology (Cambridge, UK). Examples 1 and 3, infra, also provide illustrative methods for obtaining nucleic acid sequences that encode antibody variable domains.

Essentially any antibody sequence having a desired specificity can be used for preparing immunotoxins according to the invention. Particularly preferred are antibodies having a specificity that has been shown to be therapeutically useful. Suitable examples include, but are not limited to, antibodies that bind to tumors, such as B-cell antigens, T-cell antigens, plasma cell antigens, HLA-DR lineage antigens, MUC1, MUC2, MUC3, MUC4 and MUC16 antigens, EGP-1 antigens, EGP-2 antigens, placental alkaline phosphatase antigen, carbonic anhydrase IX, IL-6, VEGF, PIGF, ILGF, Her2/neu, tenascin, CD33, CD40, CD74, CD80, PSMA, PSA, and PAP; and antigens associated with autoimmune disease, including HLA-DR, CD27, CD40, B-cell and T-cell antigens (such as CD15, CD19, CD20, CD21, CD25, and CD22 antigens). The antigen may be an antigen associated with a B- or T-cell lymphoma or leukemia, such as CD 19, CD21, CD22, CD40, MUC1, HLA-DR, and IL-15. When the antigen is CD74 or a CD74-HLA-DR complex, a suitable antibody is LL1, or a humanized version thereof. When the antigen is CD22, a suitable antibody is LL2 or RBF4, or a humanized version thereof. When the antigen is MUC1, a suitable antibody is PAM4, or a humanized version thereof. When the antigen is a CD16, a suitable antibody is either CA-125 or Mu-9. When the antigen is EGP-1, a suitable antibody is RS7, or a humanized version thereof. When the antigen is EGP-2, suitable antibodies include RS11 or 17-1A or humanized versions thereof. Advantageously, the antibody is a rapidly internalizing antibody.

Vectors that contain, or that can be engineered to contain, antibody constant domains suitable for insertion of variable domain genes are known in the art, and such vectors also are suitable for expression of immunotoxins of the present invention. Such vectors contain the necessary control sequences necessary to initiate transcription of the encoded genes in a mammalian host cell. Such control sequences are well known in the art. See, for example, the description of the pdHL2 vector in U.S. Pat. Nos. 5,650,150 and 6,472,511, which are hereby incorporated by reference in their entireties. Alternatively, constant domain genes (CH1, CH2, CH3 and CL) can be obtained from antibody producing cells and cloned into suitable expression vectors using methods that are well known in the art.

Preparation of Immunotoxin Genes

Preparation of an immunotoxin-encoding gene according to the invention is exemplified in detail in Examples 1 and 4, infra, which are provided for illustration purposes only, and are not limiting. Briefly, PCR may be used to obtain, for example, a gene encoding an antibody light chain variable domain (or heavy chain variable domain, if desired) can be obtained using PCR methods known in the art. Appropriate restriction sites may be introduced into the PCR primers, thereby facilitating subsequent ligation of the genes with additional sequences. Similarly, a cytotoxic RNAse -encoding gene can be obtained by PCR from a suitable template, again using primers that provide convenient restriction sites. The cytotoxic RNAse gene and the variable domain gene may then be digested with suitable restriction endonucleases and ligated directly together to provide a gene encoding a variable chain-RNAse fusion protein. The cytotoxic RNAse gene is advantageously linked to the N-terminus of a variable domain gene, more advantageously to the N-terminus of the light chain variable chain gene, although the RNAse gene alternatively can be linked to the N-terminus of the heavy chain variable domain, or to the N-termini of both the heavy and light chain variable domains.

Alternatively, a suitable linker can be introduced between the variable domain gene and the cytotoxic RNAse gene using, for example, a synthetic oligonucleotide that can be prepared to contain restriction sites that are compatible with those contained in the cytotoxic RNAse and immunoglobulin genes and that provide for straightforward ligation of the cytotoxic RNAse and variable domain genes and the linker sequence. The skilled artisan will recognize that a variety of linkers are suitable for use in the present invention. However, the linker is advantageously a linker containing hydrophilic amino acids that is 10-30 amino acids in length and that has little or no secondary or tertiary structure. Such linkers are well known in the art and are used, for example, in constructing single-chain Fv molecules. See for example, U.S. Pat. No. 4,946,778. Suitable linkers include multimers of the sequence GGGGS (SEQ ID NO:22) and the like. Other methods of preparing immunotoxin genes are described in U.S. patent application 20030099629, which is hereby incorporated by reference in its entirety.

If an immunotoxin containing an intact antibody structure is to be prepared (i.e. an immunotoxin containing light chain VL and CL domains and heavy chain VH and CH1-3 domains) the variable domain chains described above must be ligated to sequences that encode these additional constant domains. Advantageously, a vector is used that already contains suitable constant domains, for example, pdHL2 described supra. Alternatively methods of preparing suitable constant domains and ligating them to the variable domains are well known in the art. For Fab fragments, only CL and CH1 domains are required. Once ligated into a suitable form, these sequences then can be inserted into suitable expression vectors prior to transfection of host cells. Expression vectors that are suitable for mammalian expression are well known in the art and are also commercially available from, for example, Invitrogen, Carlsbad, Calif.

Expression of Immunotoxins in Mammalian Cells

Once a suitable expression vector has been prepared, it is transfected into an appropriate host cell. Host cells suitable for expression of recombinant antibodies are well known in the art and include, for example, CHO cells and, advantageously, myeloma cell lines such as NSO cells. Both CHO and NSO cells are available from ATCC (Manassas, Va.). Alternative host cells particularly suitable for production of immunotoxins containing human antibody sequences is Karpas 707H line described in Karpas et al., *Proc. Natl. Acad. Sci USA* 98:1799 (2001). Transfection can be achieved by well-known methods, for example, electroporation, lipofection, and DEAE-dextran-mediated transfection. Advantageously, the expression vector contains a selection marker, for example, DHFR, and the host cell is DHFR⁻. The cells are cultured in the presence of a selection agent (for example methotrexate when the selection marker is DHFR). Positive clones may be confirmed, for example, by ELISA methods using an antibody that specifically binds the cytotoxic RNAse moiety of the immunotoxin. Positive clones may be frozen for later growth, or may be expanded directly. When a culture of positive clones is grown in a suitable medium, such as complete HSFM medium, the culture supernatant, which contains the imunotoxin, is collected.

Purification of Immunotoxin

The immunotoxin may readily be purified using methods that are well known in the art. For example, affinity purification may be used. For immunotoxins containing a complete antibody structure, Protein A affinity purification may be used to provide the pure immunotoxin in a single purification step. Additional purification steps, if required, can be carried out using conventional methods such as ion exchange chromatography, size exclusion chromatography, etc. The immunotoxin may be characterized by conventional methods, for example, RP-HPLC, SDS-PAGE, mass spectrometry, and Western blotting using, for example, an anti-cytotoxic RNAse antibody. Ranpirnase from Rana Pipiens contains a potential glycosylation site (see Example. 1). In the event that glycosylation of this site is undesirable, the immunotoxin may be treated with a glycosidase enzyme to remove any carbohydrate moiety that is present on the onconase. Alternatively the gene sequence encoding the RNAse may be mutated by, for example, site directed mutagenesis, to delete the glycosylation site by replacing the Asn residue via a conservative amino acid substitution. For example, the Asn at position 69 can be replaced with a glutamine (mutant N69Q) or other suitable amino acid in any of the constructs described herein. Specific examples of this glycosylation mutant include 2L-Rap(N69Q)-hLL1-r4P, 2L-Rap(N69Q)-hRS7 and 2L-Rap(N69Q)-hLL2.

Therapeutic Methods Using Cytotoxic RNAse Immunotoxins

The immunotoxins described herein may be formulated into pharmaceutical compositions for a wide variety of cytotoxic therapeutic modalities. These compositions may be used to target any unwanted cell type, such as cells undergoing inappropriate proliferation or activation, or can be used to treat infectious disease by targeting pathogenic microorganisms. In particular, the compositions are useful for treating a variety of cancers and autoimmune diseases. Cancers that may be treated include, for example, lymphomas, leukemias, melanomas, neuroblastomas and myelomas, sarcomas, gliomas, or carcinomas, such as breast, colorectal, ovarian, liver, gastric, colorectal, prostate, lung, kidney or pancreatic carcinomas. Autoimmune diseases that may be treated include, for example, rheumatoid arthritis, systemic lupus erythematosus, Sjögren's syndrome, acute idiopathic thrombocytopenic purpura, chronic idiopathic thrombocytopenic purpura, dermatomyositis, Sydenham's chorea, myasthenia gravis, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, multiple sclerosis, sarcoidosis, ulcerative colitis, erythema multiforme, IgA nephropathy, polyarteritis nodosa, ankylosing spondylitis, Goodpasture's syndrome, thromboangitis ubiterans, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

The compositions of the present invention also are useful for the therapeutic treatment of infections, where the immunoglubulin component of the immunotoxin specifically binds to a disease-causing microorganism. In the context of the present invention a disease-causing microorganism includes pathogenic bacteria, viruses, fungi and diverse parasites, and the antibody can target these microorganisms, their products or antigens associated with their lesions. Examples of microorganisms include, but are not limited to:

*Streptococcus agalactiae, Legionella pneumophilia, Streptococcus pyogenes, Escherichia coli, Neisseria gonorrhosae, Neisseria meningitidis, Pneumococcus*, Hemophilis influenzae B, *Treponema pallidum*, Lyme disease spirochetes, *Pseudomonas aeruginosa, Mycobacterium leprae, Brucella abortus, Mycobacterium tuberculosis*, Tetanus toxin, HIV-1,-2,-3, Hepatitis A, B, C, D, Rabies virus, Influenza virus, Cytomegalovirus, Herpes simplex I and II, Human serum parvo-like virus, Papilloma viruses, Polyoma virus, Respiratory syncytial virus, Varicella-Zoster virus, Hepatitis B virus, Papilloma virus, Measles virus, Adenovirus, Human T-cell leukemia viruses, Epstein-Barr virus, Murine leukemia virus, Mumps virus, Vesicular stomatitis virus, Sindbis virus, Lymphocytic choriomeningitis virus, Wart virus, Blue tongue virus, Sendai virus, Feline leukemia virus, Reo virus, Polio virus, Simian virus 40, Mouse mammary tumor virus, Dengue virus, Rubella virus, protozoans, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides cord, Antimycoplasmal MAbs, Mycoplasma arthritidis, M. hyorhinis, M. orale, M. arginini, Acholeplasma laidlawii, M. salivarium, and M. pneumoniae.* Monoclonal antibodies that bind to these pathogenic microorganisms are well known in the art.

The skilled artisan will recognize that these examples are illustrative and not limiting of the present invention.

In these methods the pharmaceutical composition may be administered to the subject more than once, in an amount, for example of 0.1 to about 1000 mg per day, although more or less could be used as deemed appropriate.

Due to the proteinaceous nature of the compositions, they are particularly suitable for parenteral administration, such as intravenous or subcutaneous (or intracutaneous) administration, although the skilled artisan will recognize that other methods of delivery can be used, including methods for protein delivery that are currently being developed or that will be developed in the future, and may also include regional administration, such as in the peritoneal cavity, cranium, pleura, etc. For parenteral administration, the compositions may comprise a solution of the immunotoxin dissolved or suspended in a pharmaceutically acceptable carrier, preferably an aqueous carrier such as buffered saline. These solutions are sterile and may contain auxiliary substances such as pH adjusting and buffering agents and toxicity and isotonicity-adjusting agents.

Dosage of the immunotoxin is about 0.1 to 10 mg per patient per day, although dosages of up to 100 mg per patient per day may be used, particularly when the drug is administered locally, and not into the bloodstream. This dosage is based on the antibody fusion protein, which contains a smaller quantity of the RNAse component.

In therapeutic applications, the compositions are administered to a subject suffering from a disease, in a therapeutically cytotoxic amount, which is defined as an amount sufficient to kill cells of interest. An amount successful to accomplish this is defined as a "therapeutically effective amount." The exact amount in any given circumstance will depend on a variety of factors, including the severity of the disease and the general state of the patient's health. Single or multiple administrations of the compositions may be administered depending on the dosage required. Determination of a suitable dosage regimen is made using routine methods well known in the art.

The immunotoxins also can be used to treat populations of cells in vitro. For example, they may be used to selectively kill unwanted cell types in bone marrow prior to transplantation into a patient undergoing marrow ablation.

The present invention, thus generally described, will be understood more readily by reference to the following examples, which are provided by way of illustration and are not intended to be limiting of the present invention.

EXAMPLE 1

Expression, and Characterization of 2L-rap-hLL1-γ4P

In Example 1, rap represents ranpirnase.
Construction of PdHL-IgG4P Variant:

B13-24 cells containing an IgG4 gene were purchased from ATCC (ATCC Number CRL-11397) and genomic DNA was isolated. Briefly, cells were washed with PBS, resuspended in digestion buffer (100 mM NaCI, 10 mM Tris-HCI pH8.0, 25 mM EDTA pH8.0, 0.5% SDS, 0.1 mg/ml proteinase K) and incubated at 50° C. for 18 h. The sample was extracted with an equal volume of phenol/chloroform/isoamylalcohol and precipitated with 7.5 M $NH_4Ac$/100° /OEtOH. Genomic DNA was recovered by centrifugation and dissolved in TE buffer. Using genomic DNA as template, the IgG4 gene was amplified by PCR using the following primers.

```
Primer-SacII:  5' CCGCGGTCAC ATGGCACCAC CTCTCTTGCA
               GCTTCCACCAAGGGCCC 3' (47 mer; SEQ ID
               NO: 1);

Primer-EagI:   5' CCGGCCGTCG CACTCAT TTA CCCAGAGACA
               GGG 3' (33mer; SEQ ID NO: 2).
```

Amplified PCR product was cloned into a TOPO-TA sequencing vector (Invitrogen) and confirmed by DNA sequencing. The SacII-EagI fragment containing the heavy chain constant region of IgG1 in pdHL-hLL2 was replaced with SacII-EagI of the TOPO-TA-IgG4 plasmid to produce the pdHL2-hLL2-IgG4 (pdHL2-hLL2-γ4) vector.
$IgG_4$-Proline Mutation:

A Ser228Pro mutation was introduced in the hinge region of IgG4 to avoid formation of half-molecules. A mutated hinge region 56 bp fragment (Pstl-Stul) was synthesized (Top: 5'GAG TCC AAA TAT GGT CCC CCA TGC CCA eCG TGC CCA GGT AAG CCA ACC CAG G 3' (SEQ ID NO:3); Bottom: 5' C CTG GGT TGG CTT ACC TGG GCA CGG TGG GCA TGG GGG ACC ATA TTT GGA CTC TGC A 3'; SEQ ID NO:4), annealed and replaced with the Psti-Stul fragment of $IgG_4$. This construction resulted in a final vector pdHL2-hLL2-γ4P.
Construction of pdHL2-hLL1-γ4P:

The XbaI-HindIII fragment of pdHL2-hLL2-γ4P was replaced with the Xba-HindIII fragment of pdHL2-hLL1 containing Vk and VH regions to generate the hLL1-γ4P construct.
Construction of PdHL2-2L-rap-hLL1- y4P:

A flexible linker $(GGGGS)_3$ (SEQ ID NO:17) was used to attach the C-terminus of Rap to the N-terminus of $V_K$ of hLL 1. One rap molecule was attached at the N-terminus of each light chain Construction of the DNA for this molecule was done by PCR using the following primers:

```
P1; Leader 5' (XbaI): 5' CTC TAG ACA CAG GAC CTC
ACC ATG GGA TGG 3' (30 mer; SEQ ID NO: 5)
```

```
-continued
P2; Leader 3': 5' TGA AAC GTT AGC CAA TCC TGG GAG
TGG ACA CCT GTG GA 3' (38 mer; SEQ ID NO: 6)

P3; One 5': 5' TCC ACA GGT GTC CAC TCC CAG GAT TGG
CTA ACG TTT CA 3' (38 mer; SEQ ID NO: 7)

P4; One 3' (EcoRV): 5' AGT CAG CTG GAT ATC GGA
GCC ACC GCC TCC AGA TC 3' (35 mer; SEQ ID NO: 8)

P5; LL1-Vk 5' (EcoRV): 5' GAT CTG GAG GCG GTG GCT
CCG ATA TCC AGC TGA CT 3' (35 mer; SEQ ID NO: 9)

P6; LL1-Vk 3' (BamHI): 5' GGG ATC CAA CTG AGG AAG
CAA AGT TTA A 3' (28 mer; SEQ ID NO: 10)
```

Figure 2:
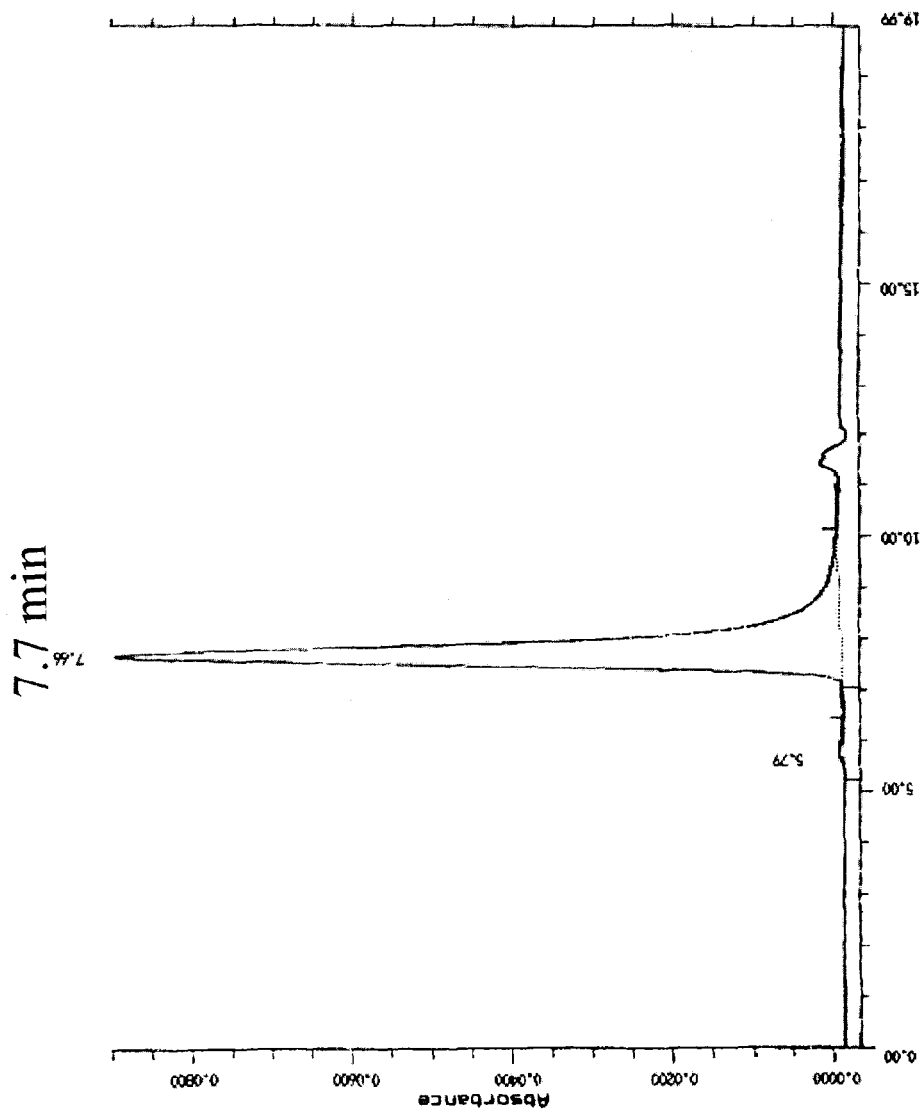
FIG. 2 shows the HPLC profile of the fusion protein secreted from the host cell. A single peak was observed at 7.7 min.

Xba-BamHI fragment of pdHL2-hLL 1-y4P was replaced with the Xba-8amHI (Xba-Leader-rap-Linker-Vk-BamHI) fragment of p8S-2L-rap-hLL 1 to complete the final vector pdHL2-2L-rap-hLL1 -y4P as illustrated in FIG. 1.
Transfection:

The vector DNA (30 µg) was linearized with SalI enzyme and transfected into NSO ($4 \times 10^6$ cells /mL) or Sp2/0-Ag14 ($5 \times 10^6$ cells/mL) myeloma cells by electroporation (450 V). Cells were grown in complete Hybridoma-SFM medium supplemented with low-IgG FBS (10%), penicillin (100 units/mL), streptomycin (100 µg/mL), L-glutamine (2 mM), sodium pyruvate (1 mM), non-essential amino acids (100 µM), and methotrexate (0.1 µM). Positive clones were screened by ELISA. Briefly, plates were coated with 50 µl of an anti-rap antibody at 5 ug/mL in PBS medium and incubated at 4° C. over night. After washing the plate with PBS and blocking with 2% BSA cell culture supernatants were added. HRP-conjugated goat anti-human $IgG_4$ antibodies were used for detection and OPD was used as a substrate for color development. Plates were read at 490 nm. Positive clones were expanded and frozen for future use. Clone C6 was identified as the best producer and used for further development.
Expression and Purification:

Cells were grown in 2 roller bottles with 500 ml media in each to terminal culture (10-20% viability) and the cells were removed by centrifugation. Culture supernatant was filtered and applied to a Protein A column, equilibrated with a 20 mM Tris-HCl/100 mM NaCl buffer (pH 8.5). Following the loading, the column was washed with a 100 mM sodium citrate buffer (pH 7.0) and eluted with 100 mM sodium citrate buffer (pH 3.5) to obtain the fusion protein. The peak containing the product was adjusted to pH 7.0 using 3 M Tris-HCl, pH 8.0 and dialyzed against 10 mM PBS buffer. Following concentration, the product was filtered through 0.22 µm filters and stored at 2-8° C. From the 1-L culture, 16 mg were recovered after purification.
Characterization of 2L-rap-hLL1-γ4P HPLC: Protein purity and concentration were checked on HPLC. A sharp single peak was observed at 7.7 min as shown in FIG. 2, with the retention time indicating the molecule was larger than IgG.

Figure 3:
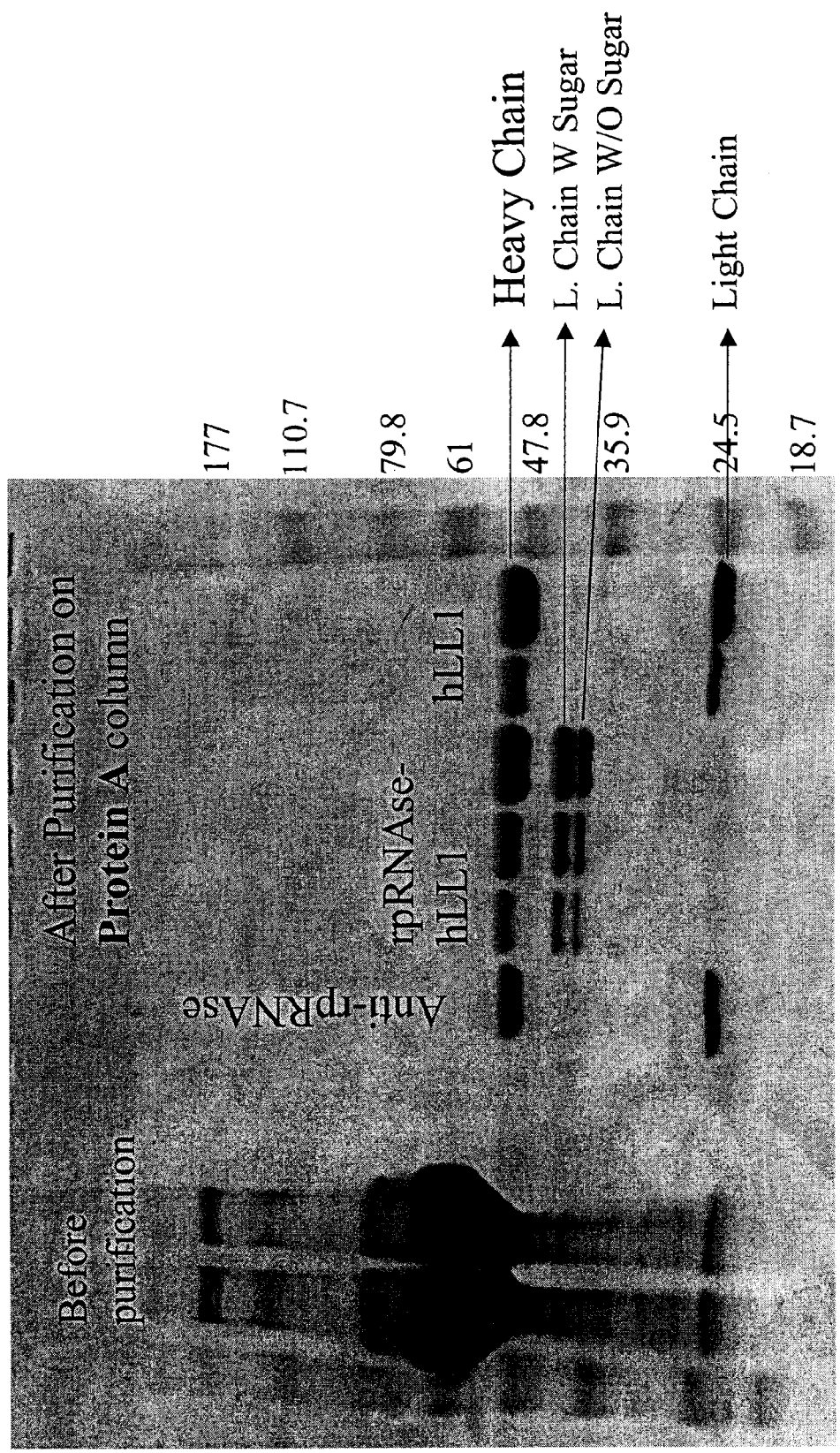
FIG. 3 shows SDS-PAGE of the secreted fusion protein. Two closely migrating light chain bands can be seen which are larger than the light chain of hLL1 alone (25 kD).

SDS-PAGE: SDS-PAGE was performed under reducing conditions using 4-20% Tris-Glycine gels (PAGEr® Gold Precast Gels, Cambrex). As shown in FIG. 3., a band related to the heavy chain of expected size about 50 kD and two bands of molecular mass about 37 and 39 kD, both larger than the light chain of hLL1 (about 25 kD), were observed. The presence of the two light chains was shown to be due to glycosylation of rap on the fusion protein (vide infra).

Figure 4A:
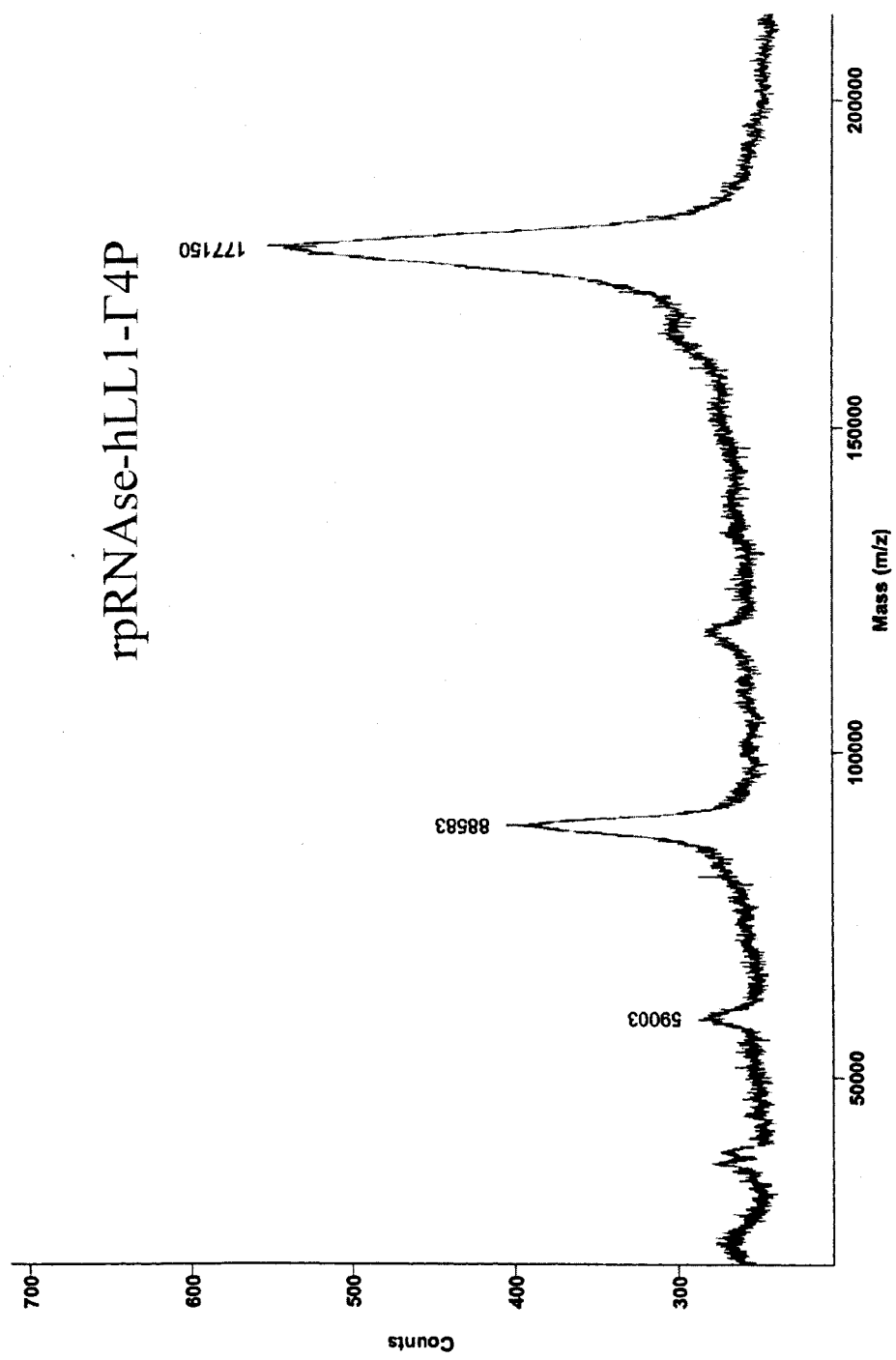
FIG. 4a shows a mass spectrum of the secreted fusion protein under native conditions: One major peak was observed corresponding to the rap-hLL1-γ4P fusion protein, with mass 177150.
Figure 4B:
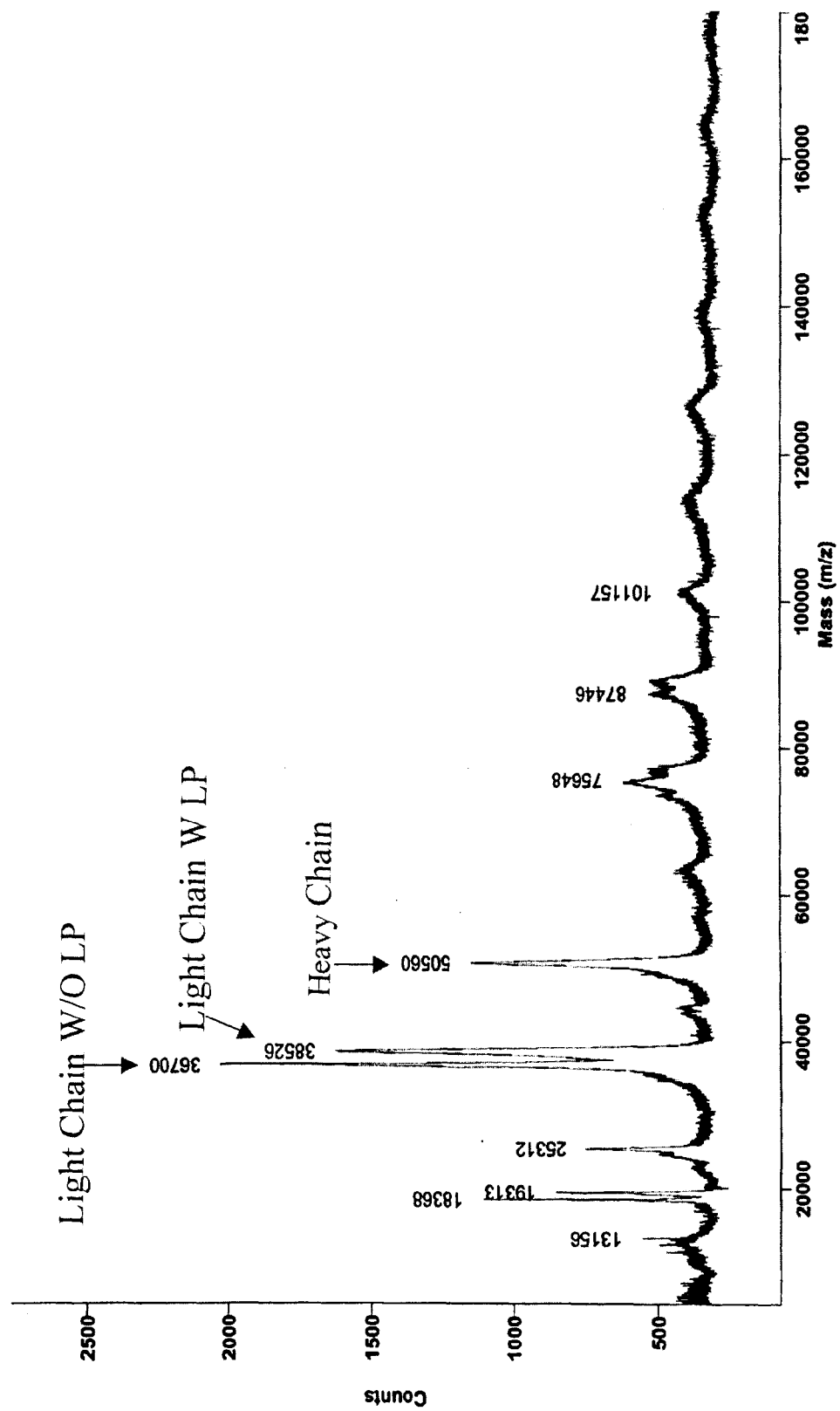
FIG. 4b shows a mass spectrum under denaturing conditions. Three major peaks can be seen corresponding to the heavy chain, and two light chains with or without sugar molecules of rap-hLL1-γ4P fusion protein.

Mass Spectrometry: Mass spectrometry was performed at The Scripps Research Institute, CA, by the MALDI-TOF method. Two samples were sent for analysis, one in the native state (1.6 mg/mL in 10 mM PBS) and the other in reduced state (1.6 mg/mL in 1 mM HEPES/10 mM DTT, pH 7.5 buffer). The native sample (FIG. 4a) showed one major peak of mass 177150, which is in good agreement with the MW of one IgG plus two raps. The reduced sample showed (FIG. 4b) three major peaks at 50560 (corresponding to the heavy chain), 38526 and 36700 (corresponding to the two light chains containing rap).

Figure 5:
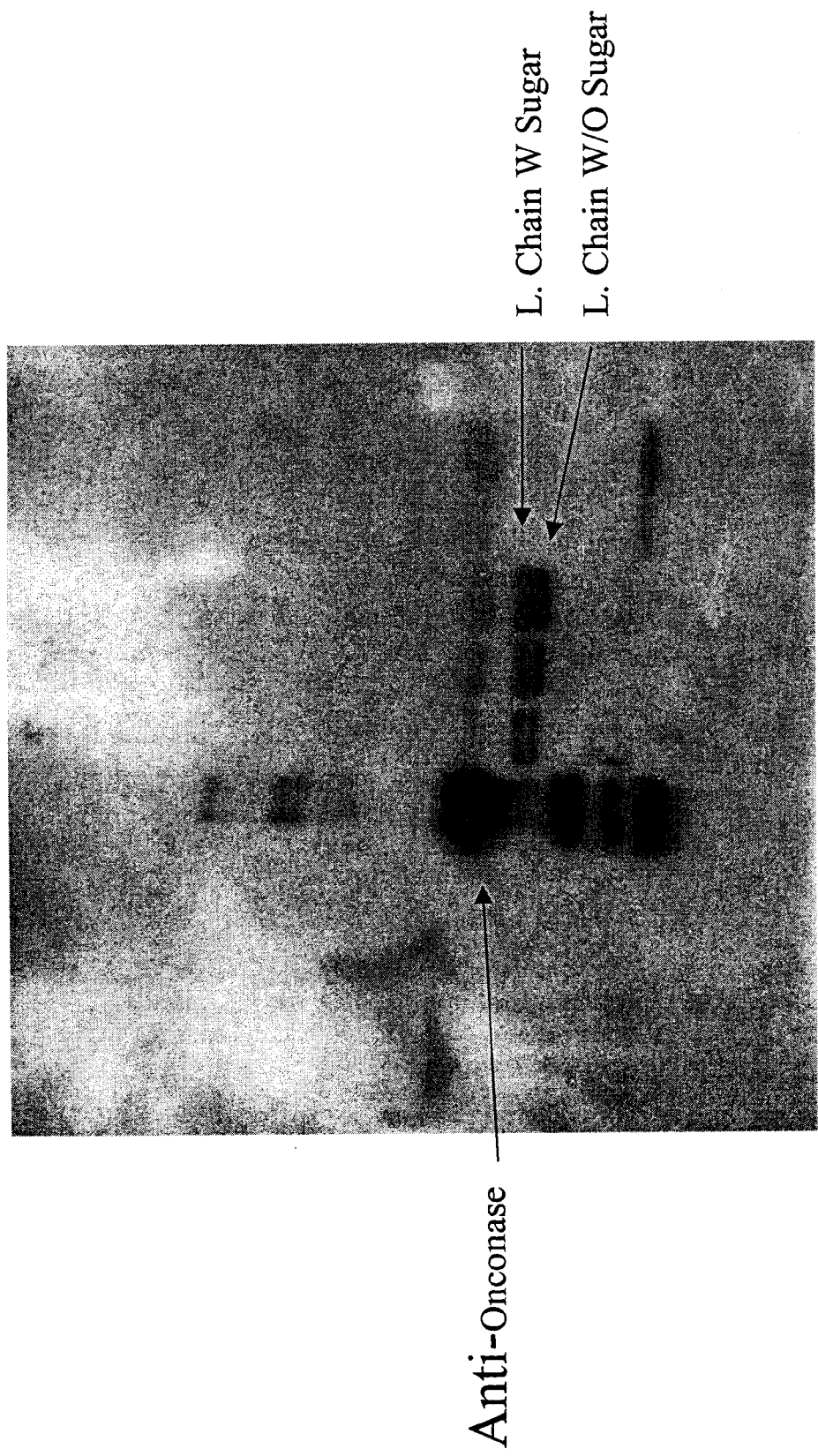
FIG. 5 shows Western blotting of the fusion protein. Light chains with and without sugar can be seen indicating both molecules contain rap.

Western Blotting: To confirm the presence of rap in the purified protein, western blotting was performed. Samples from SDS-PAGE gels under reducing condition were electro-transferred onto PVDF-Plus (Osmonics, Inc.,) membranes. After blocking with 5% BSA, mouse anti-rap antibodies were added at 1:10,000 dilution or 100 ng/ml and incubated for 1 hr. After washing, HRP-conjugated goat anti-mouse Fc antibodies were added and incubated for 1 hr. After washing six times, LumiGlo™ (Kirkegaard & Perry Laboratories) substrate was added and Kodak film was developed. As shown in FIG. 5, both bands corresponding to the fused light chains were detected on the film confirming the presence of rap on both light chains.

Figure 6:
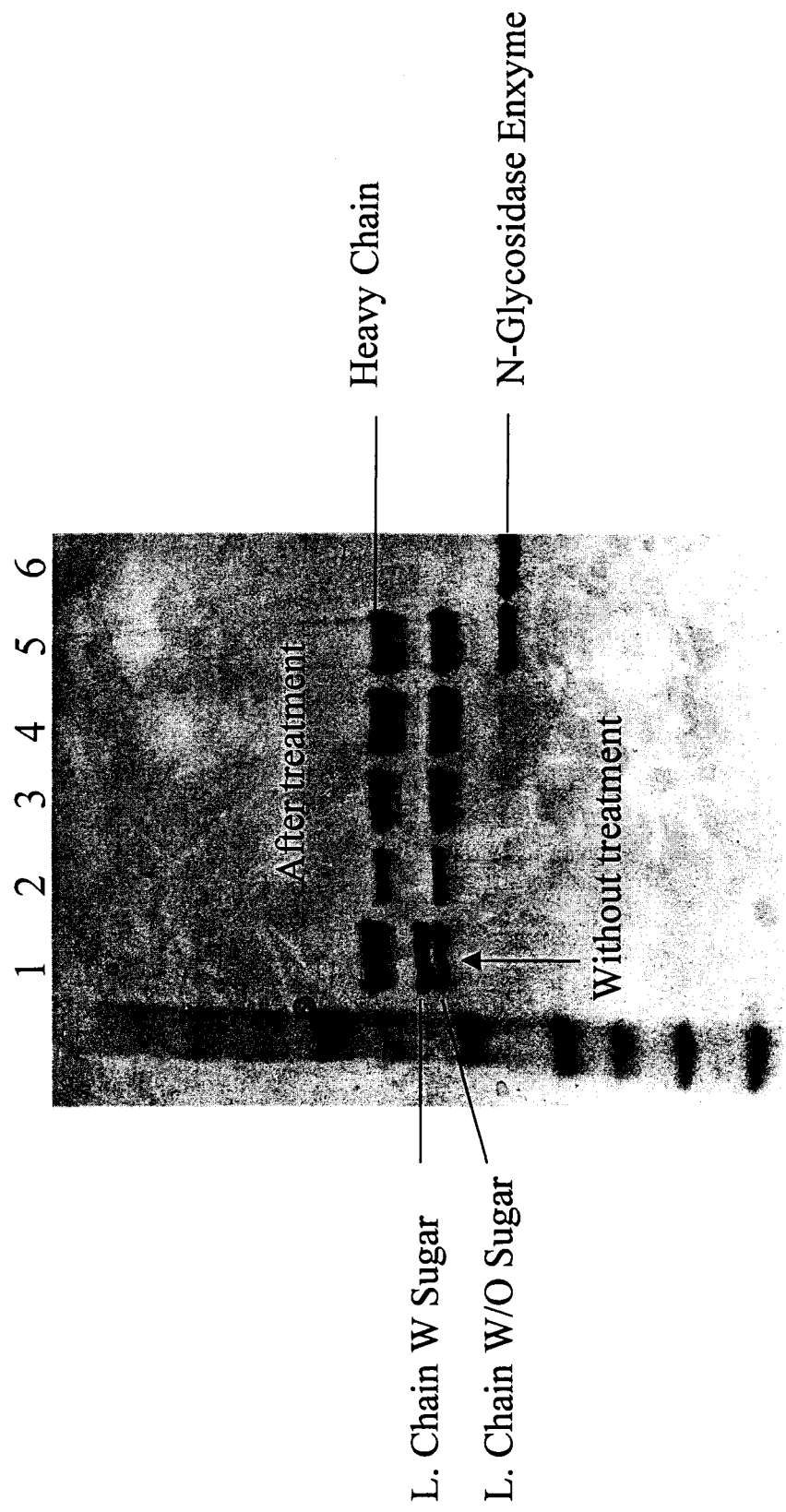
FIG. 6 shows an SDS-PAGE gel demonstrating removal of the light chain sugar molecule by N-Glycosidase treatment: Lane 1 represents untreated sample, where two light chain bands can be seen. Lanes 2-5 are samples treated with N-glycosidase enzyme. Bands corresponding to two light chains converged into one band upon sugar removal.

Treatment with N-glycosidase: As rap has a potential N-glycosylation site, Asn-X-Thr/Ser, Asn69-Val70-Thr71, the observation of two light chains with a molecular mass, difference of 2 kD might be the result of uneven glycosylation of rap. To investigate this possibility rap-hLL1 antibody was incubated with N-glycosidase (New England Biolabs) under denatured condition according to supplier's recommendations. As shown in FIG. 6, after N-glycosidase treatment the two bands corresponding to the two light chains converged into one (the faster migrating band), thus confirming that uneven distribution of carbohydrate was the reason for observation of two bands on SDS-PAGE. Further support was provided by the observation of only one Rap-fused light chain when Rap(N69Q), a variant of Rap with the glycosylation site removed, is substituted for Rap in the recombinant construct (data not shown).

Figure 7:
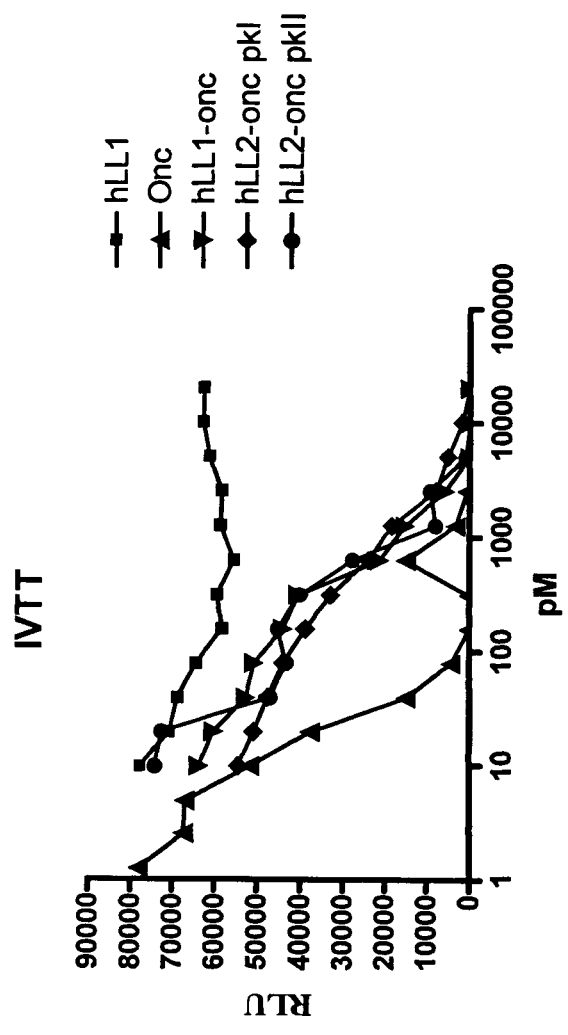
FIG. 7 shows RNAse Activity by in-vitro transcription translation assay.

Activity of rap: RNAse activity was tested by TNT® Quick Coupled Transcription/Translation System (Promega) using Bright-Glo™ Luciferase Reporter Assay system (Promega) according to supplier's recommendations. The principle for this assay was measurement of inhibition of protein synthesis (mRNA degradation) as a result of RNase activity using luciferase reporter system. Samples were prepared in different dilutions, free rap (0.001-2.5 nM), hLL1-rap (0.01-20 nM) or chemical conjugates of hLL2-rap, represented as PKI-LL2-Onc and PKII-LL2-Onc (0.01-20 nM). Each sample (5 uL) was mixed with 20 µl of TNT master mix, incubated for 2 hr at 30° C. in a 96-well plate, from which 1 µl was removed for analysis with 50 µl of Bright-Glo™ substrate. The results were shown in FIG. 7, using Excel or Prism Pad software. $EC_{50}$ values were about 300 pM for rap-hLL1 and chemical conjugates of hLL2-Onc, and 30 pM for free rap.

Figure 8:
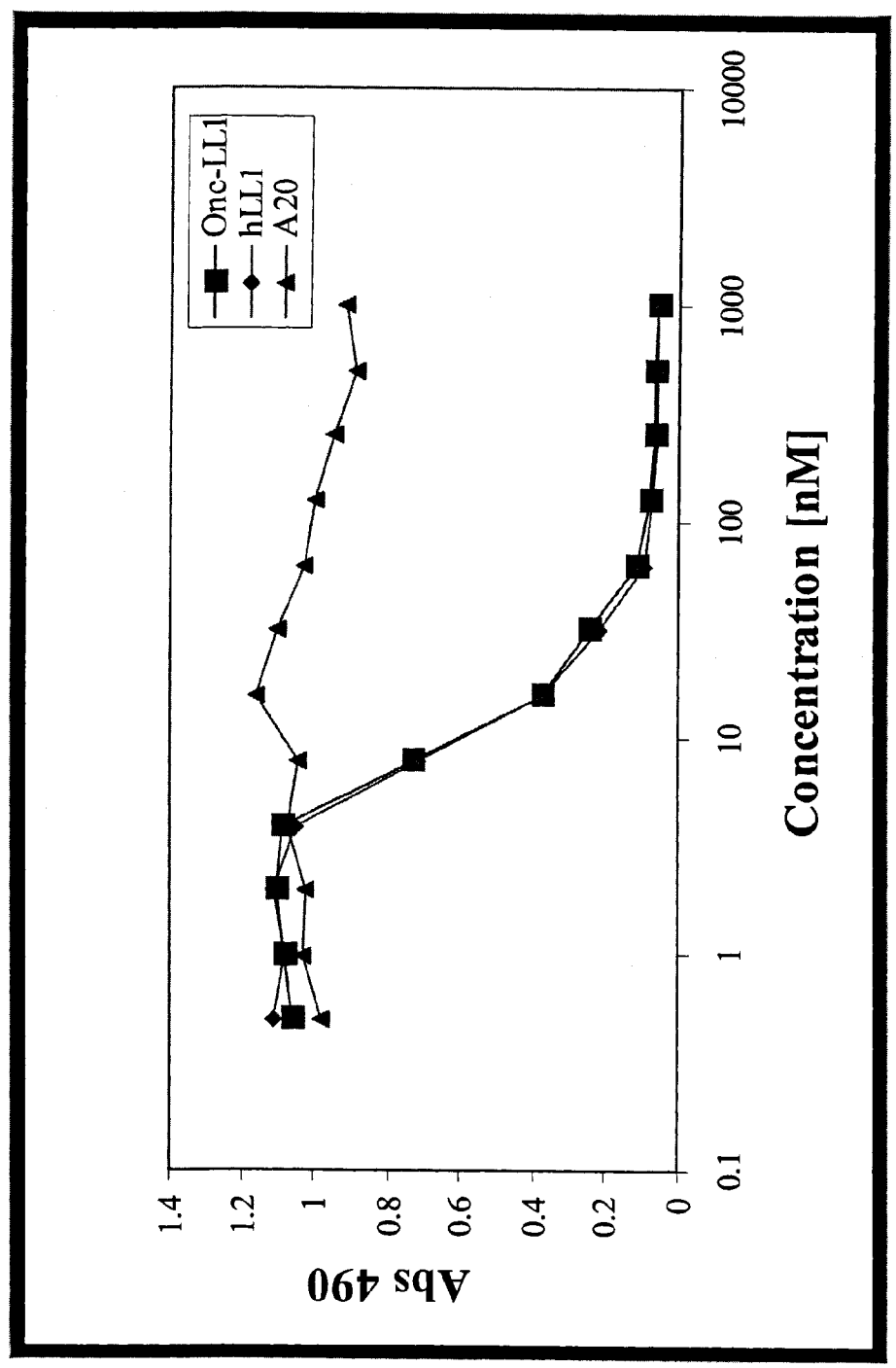
FIG. 8 shows a competition binding assay, demonstrating that hLL1 and rap-hLL1 fusion protein both have the same affinity for WP, an anti-idiotype antibody of hLL1.

Competition Binding for WP: WP, is an anti-idiotype antibody of hLL1. The affinity of rap-hLL 1 antibody in comparison with hLL1 antibody against WP was evaluated by competition binding assay. Briefly, 96-well plates were coated with 50 µl of WP at 5 ug/mL and incubated at 4° C. over night. Three types of protein samples, hLL1, rap-hLL1 or hA20 were prepared in different 2× dilutions (final concentrations range between 0.49-1000 nM), mixed with an equal volume of 2× HRP-conjugated mLL1 antibody (final dilution is 1/20,000). 50 µL of protein samples mixed with HRP-conjugated-mLL1 as described above was added to each well and incubated for 1 hr. After washing, OPD substrate containing $H_2O_2$ was added and plates were read at 490 nm. As shown in FIG. 8, protein concentration against absorbance was plotted using Excel or Prism Pad graph software. hA20 (humanized anti-CD20 antibody) was used as negative control. From FIG. 8, it is apparent that rap-hLL1 has a similar binding affinity to hLL1 and the negative control, hA20, has no affinity at all. Similar results were obtained using Raji cells as the source of antigens.

Figure 9:
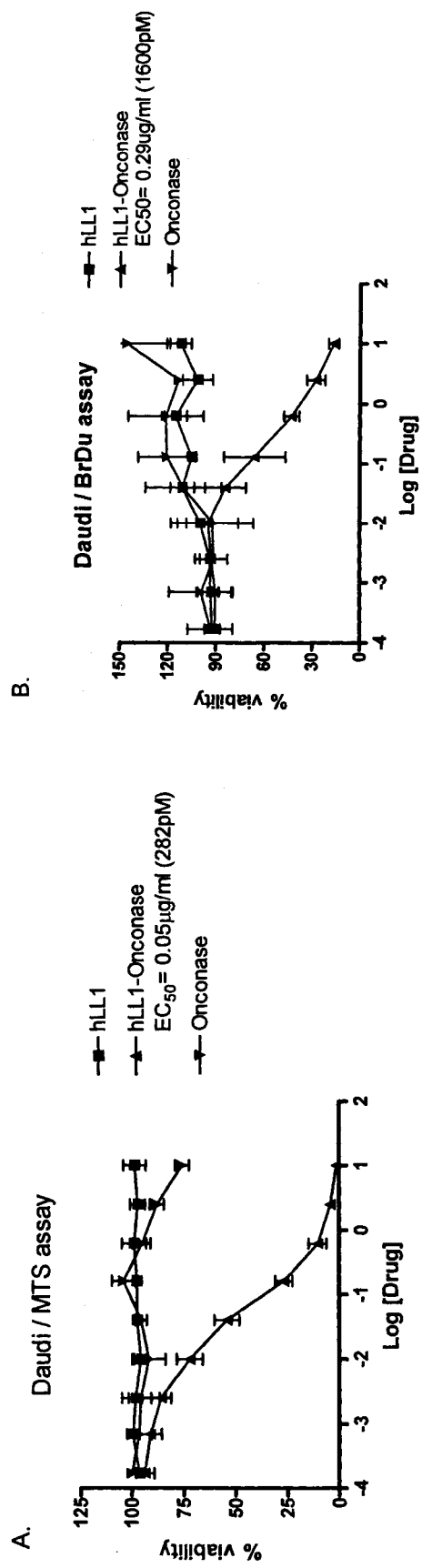
FIG. 9 shows in vitro cytotoxicity of the fusion protein in Daudi cells: A) Cytotoxicity measured by MTS assay; B) Cytotoxicity measured by BRdU assay method.
Figure 10:
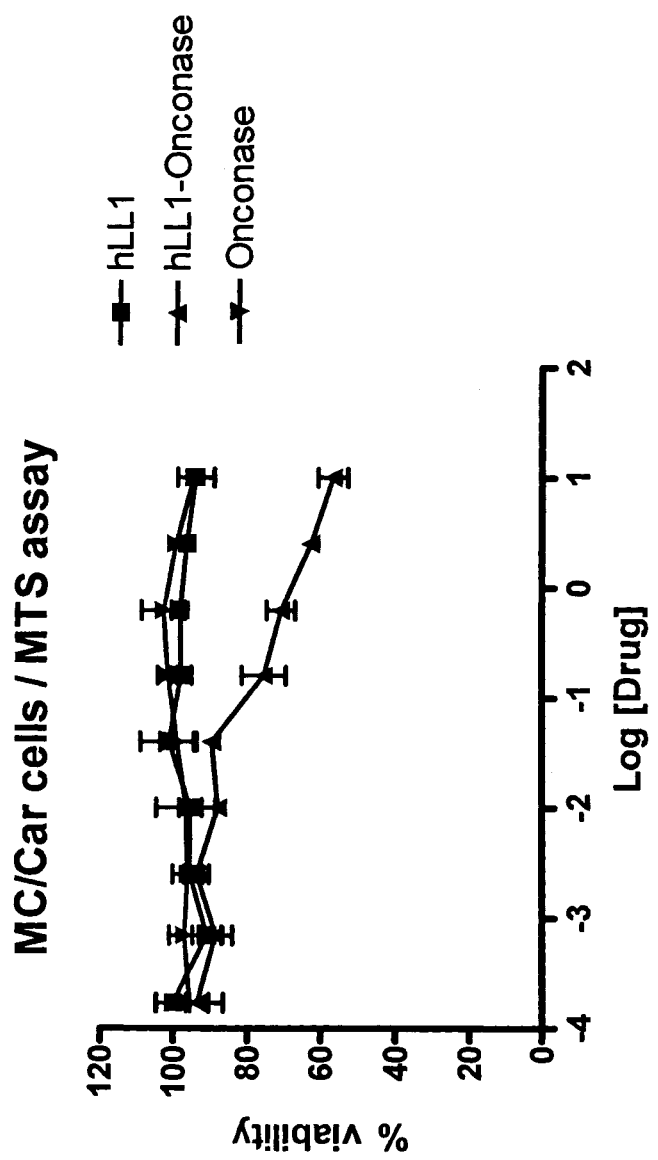
FIG. 10 shows in vitro cytotoxicity of the fusion protein in MC/CAR cells by MTS Assay.

In vitro Cytotoxicity: In vitro cytotoxicity was determined in a B-cell lymphoma cell line (Daudi), and a multiple myeloma cell line (MC/CAR). Cells (10,000 in 0.1 ml) were placed in each well of a 96-well plate. After 24 h, free hLL1, free rap or rap-hLL1 (10 µl) were added to appropriate wells, and the cells were incubated for 3 days at 37° C. in incubator. Cell proliferation was determined using the MTS tetrazolium dye reduction assay or the BrDU colorimeteric assays. Results are expressed as $EC_{50}$, which was obtained graphically using Prism Pad software. It is evident from the 1s (FIG. 9-10) that rap-hLL1 was sensitive on both, a B-cell lymphoma cell line (Daudi) and a multiple myeloma cell line (MC/CAR). rap-hLL1 was significantly more potent (cytotoxic) on Daudi cells compared to MC/CAR cells, as reflected by the $EC_{50}$ values (FIG. 9 and FIG. 10). For MC/CAR cells, an $EC_{50}$ value was not achieved at the concentrations tested. At the highest concentration (56 nM), cell viability was 57%. Future experiments will aim at determining the exact $EC_{50}$ value for rap-hLL1 on Daudi cells. hLL1 or free rap, by itself did not demonstrate cytotoxicity in either cell line.

Pharmacokinetics and biodistribution: hLL1 or 2L-Rap-hLL1-γ4P was conjugated to diethylenetriaminepentaacetic acid (DTPA) using 2-(4-isothiocyanatobezyl)DTPA (Macrocyclics, Dallas, Tex.), as described by Sharkey et al., (*Int J Cancer.* 1990; 46:79-85). to obtain DTPA-hLL1 or DTPA-2L-Rap-hLL1-γ4P, which was labeled with $^{88}$Y chloride (Los Alamos National Laboratory (Los Alamos, N. Mex.) or $^{111}$In chloride (Perkin Elmer Life Sciences, Boston, Mass.), respectively, for pharmacokinetics and biodistribution studies. Naïve female SCID mice (8 weeks old, 18-22 g) were injected intravenously with a mixture of 0.001 mCi $^{88}$Y-DTPA-hLL1 and 0.02 mCi of $^{111}$In-DTPA-2L-Rap-hLL1-γ4P, supplemented with unlabeled DTPA conjugates of hLL1 or 2L-Rap-hLL1-γ4P, so that each animal received a total dose of 10 µg each of hLL1 and 2L-Rap-hLL1-γ4P. At selected times after dosing (1, 2, 4, 16, 48, 72, 168 h), groups of 5 mice were anesthetized and a blood sample was withdrawn by cardiac puncture. Major tissues were removed, weighed, and placed in containers. Blood samples and tissues were counted in a calibrated gamma counter, Minaxi λ Auto-Gamma® 5000 series gamma counter (Packard Instrument Company; Downers Grove, Ill.) for $^{111}$In (channels 120-480) and $^{88}$Y (channels 600-2000). A crossover curve was generated to correct for the back-scatter of $^{88}$Y energy into the $^{111}$In counting window.

In vivo toxicity: Naïve SCID or BALB/c mice were injected intravenously with various doses of 2L-Rap-hLL1-γ4P ranging from 25 to 400 µg/mouse, and monitored daily for visible signs of toxicity and body weight loss. The maximum tolerated dose (MTD) was defined as the highest dose at which no death occurred, and body weight loss was ≤20% of pretreatment animal weight (approximately 20 g). Animals that experienced toxic effects were sacrificed, harvested and subjected to histopathological analysis. In naïve SCID mice, a single intravenous dose of 100, 150, 200, 250, 300 or 400 µg of 2L-Rap-hLL1-γ4P resulted in severe weight loss and death of the animals, but all mice survived a dose of 25 or 50 µg (Table 2). In BALB/c mice, all mice survived a single intravenous dose of 30 or 50 µg of 2L-Rap-hLL1-γ4P, but not 100 or 200 µg (Table 2). In another experiment, a 75 µg-dose of 2L-Rap-hLL1-γ4P was found toxic to SCID mice (data not shown). Therefore, the MTD of 2L-Rap-hLL1-γ4P given as a single bolus injection is between 50 and 75 µg in SCID mice and between 50 and 100 µg in BALB/c mice. Gross pathological examination of the dead or sacrificed mice indicated severe liver and spleen toxicity. The liver was pale in color and the spleen was shriveled and smaller than the usual size. Histopathologic examination revealed hepatic and splenic necrosis. Serum samples of the representative mice had elevated levels of alanine aminotransferase (ALT), asparatate aminotransferase (AST) and total bilirubin, suggesting significant liver toxicity at these high doses.

Data analysis: For in vitro cytotoxicity studies, dose-response curves were generated from the mean of triplicate determinations, and 50% inhibitory concentration ($IC_{50}$) values were obtained using the GraphPad Prism software (Advanced Graphics Software, Encinitas, Calif.). Pharmacokinetic data were analyzed using the standard algorithms of noncompartmental analysis program WinNonlin, Version 4.1 (Pharsight, Mountain View, Calif.). The program calculates area under the curve (AUC) using the linear trapezoidal rule with a linear interpolation. The elimination rate constant ($k_\beta$) was computed from the terminal half-life ($t_{1/2\ \beta}$) assuming first order kinetics. Survival studies were analyzed using Kaplan-Meier plots (log-rank analysis) with GraphPad Prism software. Differences were considered significant at $P<0.05$.

Figure 11:
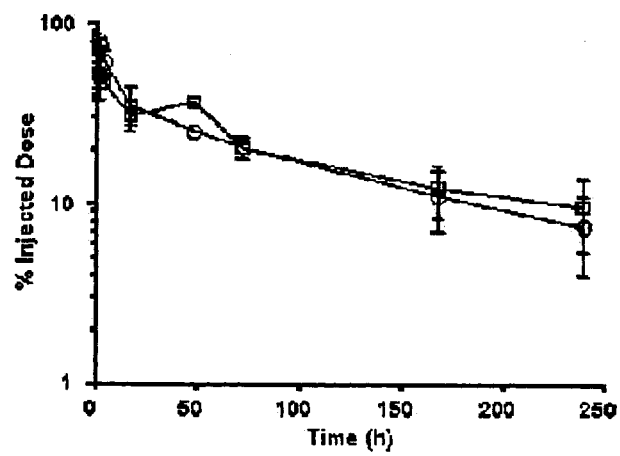
FIG. 11 shows blood clearance of 2L-Rap-hLL1-γ4P in naïve SCID mice. Naïve SCID mice were co-injected intravenously with $^{88}$Y-DTPA-hLL1 (○) and $^{111}$In-DTPA-2L-Rap-hLL1-γ4P (□). At selected times after dosing, mice were bled by cardiac puncture and a blood sample was counted for radioactivity. Data represent mean±S.D. of injected dose in blood (n=3).

Pharmacokinetic and biodistribution data: The pharmacokinetics and biodistribution of radiolabeled hLL1 and 2L-Rap-hLL1-γ4P were determined in naïve SCID mice. hLL1 and 2L-Rap-hLL1-γ4P were conjugated with DTPA and traced labeled with $^{88}$Y and $^{111}$In, respectively. As shown in FIG. 11, $^{111}$In-labeled 2L-Rap-hLL1-γ4P exhibits similar biphasic clearance from blood as $^{88}$Y-labeled hLL1, characterized by an initial rapid redistribution (α) and a later slower elimination (β) phases. A slightly shorter α half-life was observed for 2L-Rap-hLL1-γ4P (5.1 h), compared with hLL1 (4 h). Data points beyond 5 h were used to compute $t_{1/2\ \beta}$, $k_\beta$, AUC, mean residence time (MRT), apparent volume of distribution (Vd), and rate of clearance (Cl), and the values of these parameters are shown in Table 1. Tissue uptake of $^{111}$In-labeled 2L-Rap-hLL1-γ4P was similar to that of $^{88}$Y-labeled hLL1 (data not shown).

TABLE 1

Pharmacokinetic parameters determined for 2L-Rap-hLL1-γ4P and hLL1 in SCID mice using radiolabeled DTPA-conjugates

| Parameter | Unit | $^{88}$Y-DTPA-hLL1 | $^{111}$In-DTPA-2L-Rap-hLL1-y4P |
|---|---|---|---|
| $T_{1/2,\ \beta}$ | h | 103 | 113 |
| $k_\beta$ | 1/h | 0.0067 | 0.0061 |
| Cl | mL/h | 0.025 | 0.024 |
| Vd | mL | 3.8 | 3.9 |
| MRT | h | 140 | 156 |
| AUC | h*µg/mL | 393 | 418 |

In vivo toxicity In naïve SCID mice, a single intravenous dose of 100, 150, 200, 250, 300 or 400 µg of 2L-Rap-hLL1-γ4P resulted in severe weight loss and death of the animals, but all mice survived a dose of 25 or 50 µg (Table 2). In BALB/c mice, all mice survived a single intravenous dose of 30 or 50 µg of 2L-Rap-hLL1-γ4P, but not 100 or 200 µg (Table 2). In another experiment, a 75 µg-dose of 2L-Rap-hLL1-γ4P was found toxic to SCID mice (data not shown). Therefore, the MTD of 2L-Rap-hLL1-γ4P given as a single bolus injection is between 50 and 75 µg in SCID mice and between 50 and 100 µg in BALB/c mice. Gross pathological examination of the dead or sacrificed mice indicated severe liver and spleen toxicity. The liver was pale in color and the spleen was shriveled and smaller than the usual size. Histopathologic examination revealed hepatic and splenic necrosis. Serum samples of the representative mice had elevated levels of alanine aminotransferase (ALT), asparatate aminotransferase (AST) and total bilirubin, suggesting significant liver toxicity at these high doses.

TABLE 2

In vivo toxicity of 2L-Rap-hLL1-γ4P

| SCID | | BALB/c | |
|---|---|---|---|
| Dose (µg) | Survivors/Total | Dose (µg) | Survivors/Total |
| 25 | 3/3 | 30 | 5/5 |
| 50 | 4/4 | 50 | 5/5 |
| 100 | 0/4 | 100 | 1/5 |
| 150 | 0/4 | 200 | 0/5 |
| 200 | 0/4 | | |
| 250 | 0/4 | | |
| 300 | 0/4 | | |
| 400 | 0/3 | | |

Therapeutic Efficacy in Tumor-Bearing Mice

Therapeutic efficacy in tumor-bearing mice: Female SCID mice (8 weeks old, 18-22 g), 8 to 9 per group, were injected intravenously with $1.5 \times 10^7$ Daudi cells and received treatments one day later. Mice were examined daily for hind leg paralysis and were weighed weekly. The animals were euthanized when they developed hind leg paralysis or lost 20% of their pretreatment weight. Each set of therapy experiments ended after 180 days.

Figure 12:
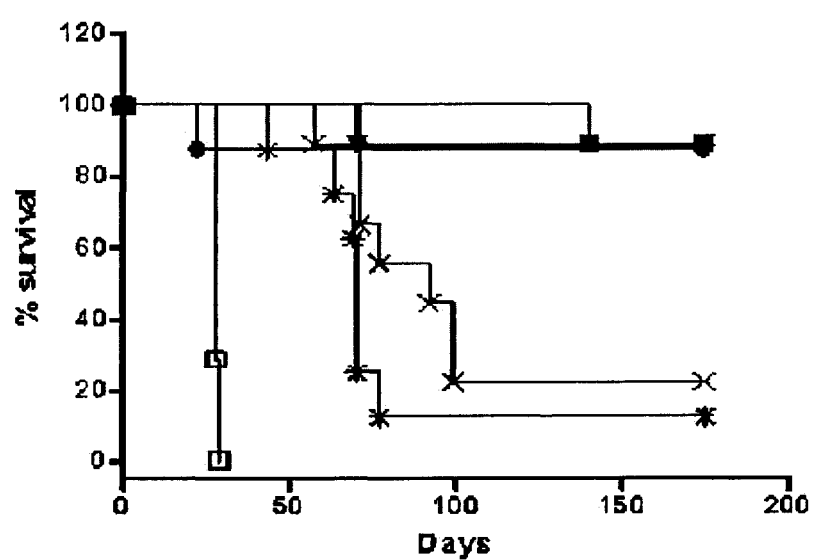
FIG. 12 shows treatment of aggressive minimal Daudi lymphoma with 2L-Rap-hLL1-γ4P or component proteins. SCID mice (8-10 mice/group) were inoculated intravenously with 1.5×10$^7$ Daudi cells. After 1 day, mice were treated with a single bolus injection of 1 μg (×), 5 μg (■), 15 μg (▲), 30 μg (▼), 40 μg (♦), or 50 μg (●) of 2L-Rap-hLL1-γ4P. Control groups were injected with component proteins equivalent to 50 μg of the immunotoxin (*) or PBS (□) only.
Figure 13:
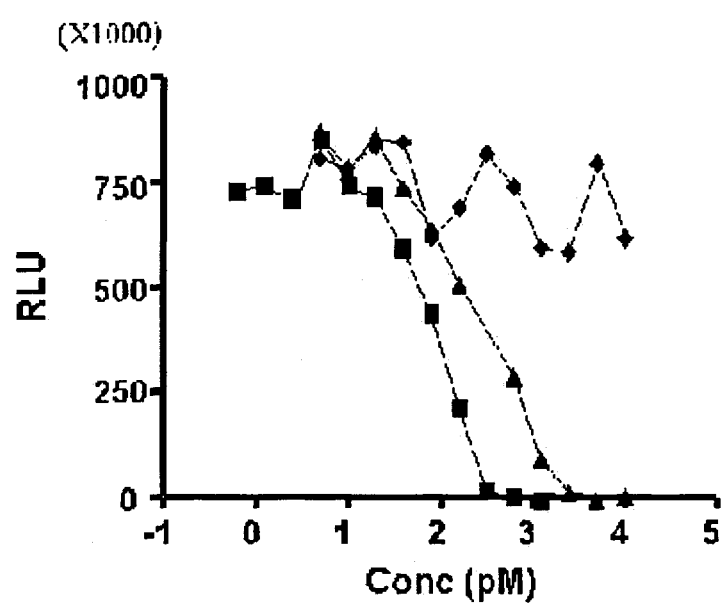
FIG. 13 shows RNase activity as measured by the in vitro transcription/translation assay. Concentrations of rRap (■), 2L-Rap-hLL1-γ4P (▲), and hLL1-γ4P (♦) were plotted against relative luminescence units (RLU).

As shown in FIG. 12, untreated mice (PBS group) all died within 30 days, with a median survival time (MST) of 28 days. The MST of the control group, which received a mixture of hLL1-γ4P (43.2 µg) and Rap (6.6 µg), representing the composition of the component proteins in 50 µg 2L-Rap-hLL1-γ4P, was 70 days (P<0.0001 vs. the PBS group). In contrast, all mice that received a single injection of either 5 or 15 µg of 2L-Rap-hLL1-γ4P were alive for more than 100 days (MST>180 days; P=0.0005 vs. components-treated group), and only one mouse was lost from each group near the end of the study. When the study was terminated after 180 days, 90% of mice receiving a single injection of 5, 15, 30, 40 or 50 µg of 2L-Rap-hLL1-γ4P were cured. It is noteworthy that the MST of mice receiving a single injection of 1 µg was 92 days, compared with 28 days of the untreated group (P<0.0001), representing a 230% increase.

EXAMPLE 2

Synthesis of PCR-Amplified DNA Encoding a Cytotoxic RNAse

A 139-mer DNA nucleotide, ONCO-N, with the sense strand sequence [5'-TGG CTA ACG TTT CAG AAG AAA CAT ATC ACG AAT ACA CGA GAT GTA GAC TGG GAC AAT ATA ATG TCT ACG AAT CTG TTT CAC TGT AAG GAT AAG AAT ACC TTT ATA TAC AGT CGG CCA GAG CCT GTA AAG GCT ATC TGT A-3' (SEQ ID NO:11)] encoding an N-terminal sequence (46 amino acids) of a recombinant cytotoxic RNAse is synthesized by an automated DNA synthesizer (Applied Biosystem 392 DNA/

RNA Synthesizer) and used as the template for PCR-amplification with the flanking primers ONNBACK [5'-AAG CTT CAT ATG CAG GAT TGG CTA ACG TTT CAG AAG AAA-3' (SEQ ID NO:12), and ONNFOR [5'CTT ACT CGC GAT AA T GCC TTT ACA GAT AGC CTT TAC AGG CTC TG-3' (SEQ ID NO:13)]. The resultant double-stranded PCR product contains cDNA sequence that encodes for 54 amino acid residues of the N-terminal half of the cytotoxic RNAse. ONNBACK contains the restriction sites HindIII (AAAGCTT) and Ndel (CATATG) to facilitate subcloning into either a staging vector or for in-frame ligation (Ndel site) into the bacterial expression vector. The Nrul site (TCGCGA) is incorporated in the ONNFOR primer to facilitate in-frame ligation with the cDNA encoding the C-terminal half of the cytotoxic RNAse.

Similarly, a 137-mer DNA nucleotide, ONCO-C, with the sense-strand sequence [TGC TGA CTA CTT CCG AGT TCT ATC TGT CCG ATT GCA ATG TGA CTT CAC GGC CCT GCA AA T AT A AGC TGA AGA AAA GCA CTA ACA AA T TTT GCG T AA CTT GCG AGA ACC AGG CTC CTG TAC ATT TCG TTG GAG TCG GG-3' (SEQ ID NO: 14)] encoding the C-terminal sequence (46 amino acids) of the cytotoxic RNAse is synthesized and PCR-amplified by the primers ONCBACK[5'-ATT ATC GCG AGT AAG AAC GTG CTG ACT ACT TCC GAG TTC TAT (SEQ ID NO: 15)- and ONCFOR[5'-TT A GGA TCC TTA GCA GCT CCC GAC TCC AAC GAA ATG TAC-3' (SEQ ID NO: 16)]. The final double-stranded PCR product contained a cDNA sequence that encoded 51 amino acids of the rest of the C-terminal half of the cytotoxic RNAse. A Nrul site allowed in-frame ligation with the N-terminal half of the PCR-amplified DNA incorporated in ONCBACK. A stop codon (shown in bold italics) and BamHI restriction sites (underlined) for subcloning into staging or expression vectors were included in the ONCFOR sequence.

The PCR-amplified DNA encoding the N- and C-terminal half of the cytotoxic RNAse after being treated with the appropriate restriction enzymes, were joined at the NruI sites and subcloned into a staging vector, e.g., pBluescript from Stratagene. The ligated sequence should encode a polypeptide of 105 amino acids with an N-terminal Met.

EXAMPLE 3

Cloning of LL2 and MN-14 V-Region Sequences and Humanization of LL2 and MN-14

The V-region sequences of hLL2 and hMN-14 have been published. Leung et al., Mol. Immunol., 32:1413 (1995); U.S. Pat. No. 5,874,540. The VK and VH sequences for LL2 and MN-14 were PCR-amplified using published methods and primers.

Sequence analysis of the PCR-amplified DNAs indicated that they encoded proteins typical of antibody VK and VH domains. A chimeric antibody constructed based on the PCR-amplified LL2 and MN-14 sequences exhibited immunoreactivity comparable to their parent antibodies, confirming the authenticity of the sequence obtained.

Sequence analysis of the LL2 antibody revealed the presence of a VK-appended N-linked glycosylation site in the framework-1 region. Mutational studies indicated that glycosylation at the VK-appended site was not required to maintain the immunoreactivity of the antibody. Without the inclusion of the FR-1 glycosylation site, REI framework sequences were used as the scaffold for grafting the light chain CDRs, and EU/NEWM for grafting the heavy chain CDRs of LL2. The immunoreactivity of the humanized LL2 (hLL2) was shown to be comparable to that of murine and chimeric LL2. The rate of internalization for LL2 was not affected by chimerization or humanization of the antibody.

EXAMPLE 4

Construction of Gene Encoding Fusion Protein of Humanized LL2 and a cytotoxic RNAse The VH and VK sequences of hLL2 were used as templates to assemble the hLL2-scFv gene by standard PCR procedures. The configuration of the gene was Met(−1)-VL-$(GGGS)_4$-VH-$(His)_6$ ($(GGGS)_4$linker and 6×His to disclosed as SEQ ID NOS 18 and 19 respectively). A Met (ATG) initiation codon at the −1 position was incorporated at the N-terminus of the VL gene, which was linked via a 16 amino acid linker $(GGGS)_6$ (SEQ ID NO: 20) to the VH domain. A tail consisting of six histidyl residues was included at the carboxyl end of the VH chain to facilitate the purification of the fusion protein via metal chelate chromatography.

The immunotoxin fusion protein gene for ranpirnase-hLL2scFv was constructed in a similar fashion by restriction digestion and ligation methods. The cDNA sequence, when expressed, encoded a fusion protein of the structure:

ranpirnase-[linker]-VL-(GGGSkVH-$(His)_6$ ($(GGGS)_4$ linker and 6×His tap disclosed as SEQ ID NOS 18 and 19, respectively).

There are a variety of linkers that can be inserted between the cytotoxic RNAse C-terminus and the VL domain N-terminus. A preferable linker is the amino acid sequence TRHRQPRGW (SEQ ID NO: 21) from the C-terminal position 273-281 of Pseudomonas exotoxin (PE). This sequence has been shown to be a recognition site for intracellular cleavage of PE into active fragments by subtilisins, with cleavage occurring between the G and W residues of the sequence. Chiron et al., J. Bioi Chem., 269:18167 (1994). Incorporation of this sequence facilitates the release of active cytotoxic RNAse after internalization of the fusion immunotoxin. Alternatively, a 13-amino acid residue spacer consisting of amino acid residues 48-60 of fragment B of Staphylococcal Protein A, used in the construction of an EDN-scFv fusion, can be used instead to allow for flexible linkage between the cytotoxic RNAse and the scFv. Tai et al., Biochemistry, 29:8024 (1990) and Rybak et al., Tumor Targeting, 1:141 (1995).

EXAMPLE 5

Construction of Gene Encoding Fusion Protein of Humanized MN-14 and Ranpirnase MN-14 scFv was produced by PCR amplification of cDNA from humanized MN-14 transfectoma. The linker used for MN-14 scFv was a 15-amino acid linker $(GGSGS)_3$ (SEQ ID NO:17 and the orientation was VL-linker-VH' After confirmation of the DNA sequences, the single chain construct is subcloned into a eukaryotic expression vector as described in Example 1 and transfected into an appropriate mammalian host cell for expression.

Another single chain construct also was made. This was made with the opposite 5'-3' orientation of the heavy and light chains, was assembled in pCANTABE5E (Pharmacia Biotech, Piscataway, N.J.) and expressed in phage. Specific binding of recombinant phage expressing this scFv was demonstrated by ELISA.

The V$_L$-linker-V sequence was used for construction of ranpirnase-MN-14 fusion protein, as diagrammed below. The DNA fragment encoding ranpirnase was obtained according to Example 1. A 23-amino acid linker was used between the ranpirnase sequence and the scFv. Kurucz et al. (1995). Alternatively, the (GGSGS)$_3$ (SEQ ID NO:17) linker which was used in construction of the MN-14 scFv described above was used. A preferred configuration of the fusion protein was:

ranpirnase-linker-V$_L$-(GGSGS)$_3$-V$_H$ ((GGSGS)$_3$ linker disclosed as SEQ ID NO:17).

The contents of all patents and other references cited herein are incorporated by reference in their entirety.

What is claimed is:

1. An immunotoxin comprising:
   (a) a first fusion polypeptide, wherein said fusion polypeptide comprises a non-mammalian ribonuclease fused to a first immunoglobulin variable domain and
   (b) a second polypeptide comprising a second immunoglobulin variable domain, wherein said first and second immunoglobulin variable domains comprise the CDRs of the immunoglobulin heavy and light chain of an antibody which together form an antigen binding site
   wherein said non-mammalian ribonuclease is fused to the N-terminus of said first immunoglobulin variable domain, wherein said non-mammalian ribonuclease bears an N-terminal pyroglutamate residue, and wherein the first immunoglobulin variable domain is a light chain variable domain
   wherein said non-mammalian ribonuclease is ranpirnase or a conservatively modified variant thereof and wherein the immunotoxin is glycosylated.

2. The immunotoxin according to claim 1, wherein said non-mammalian ribonuclease is Rap (N69Q) ranpirnase.

3. The immunotoxin according to claim 1, wherein the antibody binds to an antigen selected from the group consisting of CD22, EGP-1, CD74, and CEA.

4. The immunotoxin according to claim 1, wherein the antibody is selected from the group consisting of hLL2, hRS7, hLL1 and hMN 14.

5. The immunotoxin according to claim 1, wherein the immunotoxin is glycosylated on the CH2 domain.

6. The immunotoxin according to claim 1, wherein the non-mammalian ribonuclease is from *Rana pipiens*.

7. The immunotoxin according to claim 1 wherein said variable domains are humanized or human domains.

8. The immunotoxin according to claim 1, wherein the non-mammalian ribonuclease is fused only to the N-terminus of said first immunoglobulin variable domain.

9. A method of preparing an immunotoxin comprising culturing a mammalian host cell, wherein said host cell is transfected with (a) a first nucleic acid sequence encoding a fusion polypeptide, wherein said fusion polypeptide comprises a non-mammalian ribonuclease fused to a first immunoglobulin variable domain and (b) a second nucleic acid sequence encoding a second polypeptide comprising a second immunoglobulin variable domain, wherein said first and second immunoglobulin variable domains together form an antigen binding site; wherein said non-mammalian ribonuclease is fused to the N-terminus of said first immunoglobulin variable domain, wherein said non-mammalian ribonuclease bears an N-terminal pyroglutamate residue, and wherein the first immunoglobulin variable domain is a light chain variable domain, wherein said non-mammalian ribonuclease is ranpirnase or a conservatively modified variant thereof and wherein the immunotoxin is glycosylated.

10. The method according to claim 9, wherein said fusion polypeptide and said second immunoglobulin variable domain are produced as separate molecules in said host cell.

11. The method according to claim 9, wherein said fusion polypeptide further comprises a CL domain and said second polypeptide further comprises a CH1 domain; or a CH1 domain, a hinge, a CH2 domain and a CH3 domain; or alternatively said fusion polypeptide further comprises a CH1 domain; or a CH1 domain, a hinge, a CH2 domain and a CH3 domain, and said second polypeptide comprises a CL domain.

12. The method according to claim 9, wherein said immunotoxin is glycosylated on the CH2 domain.

13. The method according to claim 9, wherein said variable domains are humanized or human domains.

14. The method according to claim 9, wherein said first and second nucleic acid sequences are contained within a pdHL2 vector.

15. The method according to claim 9, wherein said first and second immunoglobulin domains are IgG4 domains containing a mutation that inhibits formation of half-molecules.

16. The method according to claim 9, wherein said non-mammalian ribonuclease is Rap (N69Q) ranpirnase.

* * * * *

SEQUENCE LISTING

```
<160> NUMBER OF SEQ ID NOS: 22

<210> SEQ ID NO 1
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccgcggtcac atggcaccac ctctcttgca gcttccacca agggccc                47

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccggccgtcg cactcattta cccagagaca ggg                               33

<210> SEQ ID NO 3
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gagtccaaat atggtccccc atgcccaccg tgcccaggta agccaaccca gg          52

<210> SEQ ID NO 4
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cctgggttgg cttacctggg cacggtgggc atgggggacc atatttggac tctgca      56

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctctagacac aggacctcac catgggatgg                                   30
```

```
<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgaaacgtta gccaatcctg ggagtggaca cctgtgga                              38

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7 tccacaggt gtccactccc aggattggct aacgtttca                              38

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agtcagctgg atatcggagc caccgcctcc agatc                                 35

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gatctggagg cggtggctcc gatatccagc tgact                                 35

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggatccaac tgaggaagca aagtttaa                                         28

<210> SEQ ID NO 11
<211> LENGTH: 139
<212> TYPE: DNA
<213> ORGANISM: Artificial Sequence
<220> FEATURE:
<223> OTHER INFORMATION: Description of Artificial Sequence: Synthetic
      coding nucleotide sequence

<400> SEQUENCE: 11
tggctaacgt tcagaagaa acatatcacg aatacacgag atgtagactg gacaatata        60 atgtctacga atctgtttca ctgtaaggat aagaatacct ttatatacag tcggccagag     120
```
cctgtaaagg ctatctgta                                              139

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aagcttcata tgcaggattg gctaacgttt cagaagaaa                         39

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cttactcgcg ataatgcctt tacagatagc ctttacaggc tctg                   44

<210> SEQ ID NO 14
<211> LENGTH: 137
<212> TYPE: DNA
<213> ORGANISM: Artificial Sequence
<220> FEATURE:
<223> OTHER INFORMATION: Description of Artificial Sequence: Synthetic
      coding nucleotide sequence

<400> SEQUENCE: 14
tgctgactac ttccgagttc tatctgtccg attgcaatgt gacttcacgg ccctgcaaat   60
ataagctgaa gaaaagcact aacaaatttt gcgtaacttg cgagaaccag gctcctgtac  120
atttcgttgg agtcggg                                                137

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
attatcgcga gtaagaacgt gctgactact tccgagttct at                     42

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttaggatcct tagcagctcc cgactccaac gaaatgtac                         39

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic

```
                               linker peptide

<400> SEQUENCE: 17

Gly Gly Ser Gly Ser Gly Gly Ser Gly Ser Gly Gly Ser Gly Ser
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 18

Gly Gly Gly Ser Gly Gly Gly Ser Gly Gly Ser Gly Gly Gly Ser
1               5                   10                  15

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 19

His His His His His His
1               5

<210> SEQ ID NO 20
<211> LENGTH: 24
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 20

Gly Gly Gly Ser Gly Gly Gly Ser Gly Gly Ser Gly Gly Gly Ser
1               5                   10                  15

Gly Gly Gly Ser Gly Gly Gly Ser
            20

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Arg His Arg Gln Pro Arg Gly Trp
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide
```

```
<400> SEQUENCE: 22

Gly Gly Gly Gly Ser
1               5
```